US012690820B2

(12) United States Patent
Gouze

(10) Patent No.: US 12,690,820 B2
(45) Date of Patent: Jul. 28, 2026

(54) DETECTION OF PROLONGED POSTPRANDIAL HYPERGLYCEMIA, GLYCEMIC PEAK LINEAR PREDICTION AND INSULIN DELIVERY ADJUSTMENT

(71) Applicant: M-DT-1, Roquefort-les-Pins (FR)

(72) Inventor: Jean Noel Gouze, Roquefort-les-Pins (FR)

(73) Assignee: M-DT-1, Roquefort-les-Pins (FR)

( * ) Notice: Subject to any disclaimer, the term of this patent is extended or adjusted under 35 U.S.C. 154(b) by 345 days.

(21) Appl. No.: 18/554,579

(22) PCT Filed: Apr. 14, 2022

(86) PCT No.: PCT/EP2022/060002
§ 371 (c)(1),
(2) Date: Oct. 9, 2023

(87) PCT Pub. No.: WO2022/219115
PCT Pub. Date: Oct. 20, 2022

(65) Prior Publication Data
US 2024/0188900 A1 Jun. 13, 2024

(30) Foreign Application Priority Data
Apr. 16, 2021 (EP) .................................... 21169024

(51) Int. Cl.
*A61B 5/00* (2006.01)
*A61B 5/145* (2006.01)
*G16H 50/30* (2018.01)

(52) U.S. Cl.
CPC ........ *A61B 5/7275* (2013.01); *A61B 5/14532* (2013.01); *A61B 5/4839* (2013.01); *A61B 5/7246* (2013.01); *G16H 50/30* (2018.01)

(58) Field of Classification Search
None
See application file for complete search history.

(56) References Cited

U.S. PATENT DOCUMENTS

2010/0145725 A1* 6/2010 Alferness ............... G16H 50/20
705/3
2010/0262434 A1* 10/2010 Shaya .................. A61B 5/7475
705/3

(Continued)

FOREIGN PATENT DOCUMENTS

WO 2021026004 A1 2/2021

OTHER PUBLICATIONS

International Search Report for PCT/EP2022/060002 mailed Jun. 29, 2022, 5 pages.

(Continued)

*Primary Examiner* — Etsub D Berhanu
(74) *Attorney, Agent, or Firm* — NIXON & VANDERHYE

(57) ABSTRACT

Postprandial glycemic peak can be predicted from a preprandial glucose measurement and a postprandial measurement few minutes after a meal defining a glucose rise rate. A linear relationship gives the peak glucose increase from the glucose rise rate. Hence, peak characteristics are obtained. Accurate peak prediction given known error margins is strongly correlated with healthy two-hour postprandial hyperglycemia profiles. Consequently, accuracy of the peak predictions is used to infer risks of postprandial hyperglycemia substantially prolonged beyond two hours. Appropriate correction of insulin intradermic delivery is then taken early in the process.

20 Claims, 8 Drawing Sheets

(56)  References Cited

U.S. PATENT DOCUMENTS

| 2018/0169332 | A1* | 6/2018 | Sadeghzadeh | ......... G16H 50/20 |
| 2018/0271455 | A1 | 9/2018 | Zhong et al. | |
| 2020/0170578 | A1 | 6/2020 | Park et al. | |
| 2020/0375549 | A1 | 12/2020 | Wexler et al. | |
| 2021/0104173 | A1* | 4/2021 | Pauley | ................... G16H 20/10 |

OTHER PUBLICATIONS

Written Opinion of the ISA for PCT/EP2022/060002 mailed Jun. 29, 2022, 7 pages.

Rozier Eric W D: "Fraise: A framework for predicting peak post-prandial blood glucose using personalized data-driven modeling", 2017 IEEE International Conference on Bioinformatics and Bio-medicine (BIBM), IEEE, Nov. 13, 2017, pp. 1097-1104, XP033278465 [Submission Pending].

Daenen S et al, "Peak-time determination of post-meal glucose excursions in insulin-treated diabetic patients," Diabetes & Metabo-lism, Paris, Amsterdam, NL, vol. 36, No. 2, Apr. 1, 2010, pp. 165-169 [Submission Pending].

* cited by examiner

DETECTION OF PROLONGED POSTPRANDIAL HYPERGLYCEMIA, GLYCEMIC PEAK LINEAR PREDICTION AND INSULIN DELIVERY ADJUSTMENT

CROSS-REFERENCE TO RELATED APPLICATIONS

This application is the U.S. national phase of International Application No. PCT/EP2022/060002 filed Apr. 14, 2022 which designated the U.S. and claims priority to EP 21169024.3 filed Apr. 16, 2021, the entire contents of each of which are hereby incorporated by reference.

FIELD OF THE INVENTION

The present invention relates to the field of computer technology, and in particular to computer-aided methods and apparatuses for detecting prolonged postprandial hyperglycemia, predicting postprandial glycemic peaks and assisting diabetic patients to dynamically adjust anti-diabetic drug, a storage medium and a computer device.

BACKGROUND OF THE INVENTION

Diabetes is the leading cause of death worldwide with a growing number of people living with the disease that should reach up to 580 million by 2045. Chronic hyperglycemia is the main characteristic of diabetes and is caused by defects in insulin secretion and/or insulin biological activity.

Type 1 diabetes (T1D) is due to insulin production deficiency while type 2 diabetes results from an ineffective use by the body of insulin.

Long-term complications of chronic hyperglycemia include inter alia kidney failure, neuropathy, retinopathy, cardiovascular disease and blood vessel failure.

Blood glucose levels are physiologically highly variable and are influenced by many different factors such as carbohydrate uptake, hormones stimulating glucose release and/or uptake from cells and organs, but also by numerous external factors such as stress, medications, physical activity, behavior or environments.

Physiological insulin secretion is permanent over the day and constantly balances blood sugar levels.

Because carbohydrate uptake is the main contributor in blood sugar increase, pronounced secretory insulin peaks occur after meals while lower secretions occur during the rest of the day. To avoid above-mentioned long-term complications associated with chronic hyperglycemia, keeping blood sugar levels as close as possible to normal healthy range (70-120 mg/dL) represents the main goal and challenge of diabetes management.

In insulin-dependent individuals, this blood glucose management is made through the injection (or delivery) of insulin using syringes, pens or pumps several times a day.

In nondiabetic individuals, the plasma glucose concentration peaks in average one hour after the start of a meal and rarely exceeds 140 mg/dl. The return to pre-prandial levels (e.g. 80-120 mg/dL) then occurs within two to three hours after the meal.

Hyperglycemia that occurs after a meal is called postprandial hyperglycemia (PPH) and accounts for most of the overall blood sugar imbalance in insulin-dependent individuals.

Effectively controlling PPH is one of the most complicated challenges for diabetic patients as post-meal glycemic spikes are influenced by many factors despite the administration of insulin (e.g. nature of the carbohydrates ingested, presence of other nutrients, stress etc. . . . ).

The PPH can be extremely variable in height and duration from meal to meal, day to day and from individual to individual.

Although there is indisputable evidence that PPH contributes significantly to long-term damage to the body, various postprandial (PP) glycemic recommendations have been set. For instance, blood glycemic levels to be reached two hours post meal (i.e. two-hour postprandial glycemic or glucose or sugar levels) shall be lower than 140 mg/dl for the American Association of Clinical Endocrinologist, lower than 180 mg/dl for the American Diabetes Association, lower than 160-180 mg/dl for the European Association for the Study of Diabetes, and lower than 160 mg/dL for the International Diabetes Federation.

Day-to-day real life analysis of glucose profiles shows that despite the delivery of a correct amount of insulin (corresponding to the carbohydrate uptake), the postprandial glycemic peak is often prolonged for more than two hours at high glucose levels (e.g. >160 mg/dL), hence defining postprandial hyperglycemia. The duration of the PPH is extremely variable because abnormal glycemic states are randomly observed and the corrective measures to correct insulin delivery to the patient are often taken too late to maintain a healthy glycemic average value over the considered day.

A need thus exists for insulin-dependent individuals to early anticipate the evolution of their postprandial blood glucose values and early detect any risk of prolonged (i.e. two hours or more) postprandial hyperglycemia. This would help them to early take appropriate corrective measures for insulin delivery, and hence to have a better management of PPH and indirectly of the long-term blood glucose level average. Corrective measures based on personalized corrective recommendations may ensure a rapid return to normalized blood sugar levels with reduced risks of postprandial hypoglycemia.

Some modeling methods of blood glucose levels are already known and can be divided into two categories: physiological and data-driven methods. A physiological model consists in transforming known glucose metabolism in mathematical functions that can be implemented with different parameters such as addition of insulin, exercise, and emotional state. With the abundant and complete glucose profiles obtained from continuous glucose monitoring system, many studies now recommend to use data driven methods to build a prediction model, such as an autoregressive integrated moving average model-based algorithm, a real-time learning recurrent neural network, a vector regression, or a deep learning method.

Document "*Fraise: A framework for predicting peak postprandial blood glucose using personalized data-driven modeling*" (ROZIER ERIC) is known that provides a linear B spline model to estimate the future range of patient's post meal blood glucose values based on his or her planned meal.

US 2020/375549 is also known that predicts patient's future blood glucose state through the sequential use of several set of machine learning systems.

All known methods are quite complex in that they require a high number of parameters to be gathered, such as numerous blood glucose measurements, an indication of carbohydrate uptake, a tough evaluation of the patient's emotional state, and so on.

There is a need to provide simpler monitoring-based predictive method and apparatus of postprandial glycemia.

SUMMARY OF THE INVENTION

The present invention seeks to overcome some of the foregoing concerns.

Prolonged postprandial hyperglycemia can be early detected with low complexity.

The present invention seeks to provide a simpler modeling of the postprandial glycemia. In this respect, the invention proposes a computer-aided method of predicting a postprandial glycemic peak of an individual. The method comprises:

obtaining, from a glucose sensor, blood glucose level measurements of the individual, including one pre-prandial blood glucose level measurement, determining a postprandial glucose change rate from the pre-prandial blood glucose level measurement and one postprandial blood glucose level measurement, and linearly inferring a peak glucose level from the determined postprandial glucose change rate and from the pre-prandial blood glucose level measurement.

The inventor has surprisingly discovered the postprandial glycemic peak is linearly related to the postprandial glucose change rate. Hence, a precise prediction of the characteristics of the PP glycemic peak, i.e. peak value and peak occurring time, may advantageously be obtained from a limited number (i.e., two or more) measurements (to obtain the rate).

Correspondingly, the invention also proposes a computer device comprising at least one microprocessor configured for carrying out the steps of the method. The computer device comprises:

a glucose sensor configured to obtain blood glucose level measurements of an individual, including one pre-prandial blood glucose level measurement, a postprandial glycemia rate unit configured to determine a postprandial glucose change rate from the pre-prandial blood glucose level measurement and one postprandial blood glucose level measurement, and a peak determination unit configured to linearly infer a peak glucose level from the determined postprandial glucose change rate and from the pre-prandial blood glucose level measurement.

In some embodiments, the postprandial glucose change rate is determined from the pre-prandial blood glucose level measurement and only one postprandial blood glucose level measurement. Only two measurements are thus required for the prediction according to the invention.

In other embodiments, a peak glucose increase is linearly inferred from the determined postprandial glucose change rate and the peak glucose level is a sum of the measured pre-prandial glucose level with the peak glucose increase.

In yet other embodiments, a peak time is determined that is a sum of a ratio between the peak glucose increase and the postprandial glucose change rate with a pre-prandial time of the pre-prandial blood glucose level measurement.

In some embodiments, the pre-prandial blood glucose level measurement is made within a time window of five min before and after starting a meal.

In some embodiments, the postprandial blood glucose level measurement is made within a time window of 5 to 45 min after ending a meal, preferably 10-30 min, more preferably 10-20 min, even more preferably 10-15 min. The postprandial blood glucose level measurement is thus made before the glycemic peak occurs.

The present invention also proposes a method of assisting a diabetic individual, for example still to dynamically adjust an anti-diabetic treatment. The invention seeks to help insulin-dependent individuals suffering from diabetes. The method can then help to dynamically drive anti-diabetic drug adjustment, including insulin delivery adjustment. The method comprises:

obtaining, using a glucose sensor, measurements of blood glucose levels of an individual, computer-predicting a postprandial glycemic peak based on some blood glucose level measurements, determining whether additional blood glucose level measurements include a measured postprandial glycemic peak matching the predicted postprandial glycemic peak, and emitting a signal of prolonged postprandial hyperglycemia in case of negative determining.

The steps of obtaining blood glucose level measurements and of computer-predicting a postprandial glycemic peak preferably implement the above computer-aided method of predicting a postprandial glycemic peak of an individual.

The inventor has surprisingly noticed that a correct prediction (i.e. peak matching) of the postprandial glycemic peak occurs on the great majority of two-hour postprandial profiles showing a satisfying glycemia<160 mg/dL ("healthy profiles") while an incorrect prediction (i.e. peak non-matching) occurs on the great majority of two-hour postprandial hyperglycemia profiles showing a high glycemia>160 mg/dL ("hyperglycemia profiles"). Hence, risks of prolonged postprandial hyperglycemia can be early and efficiently detected based on the mere matching between the predicted peak and the actual measured peak. Indeed, as soon as a measured peak is detected or the predicted peak should have occurred, the invention allows appropriate insulin delivery adjusting measures to be taken to reduce the risks of prolonged postprandial hyperglycemia.

Correspondingly, the invention also proposes a system comprising at least one microprocessor configured for carrying out the steps of the method. The system comprises:

a glucose sensor configured to obtain measurements of blood glucose levels of an individual, a computer-aided prediction unit configured to predict a postprandial glycemic peak based on some blood glucose level measurements, a matching peak determination unit configured to determine whether additional blood glucose level measurements include a measured postprandial glycemic peak matching the predicted postprandial glycemic peak, and a signal emitting unit configured to emit a signal of prolonged postprandial hyperglycemia in case of negative determining.

Optional features of embodiments of the invention are defined in the appended claims. Some of these features are explained here below with reference to a method, while they can be transposed into device features.

In some embodiments, evaluating a matching between peaks includes determining whether a measured peak time of the measured postprandial glycemic peak equals a predicted peak time of the predicted postprandial glycemic peak given a time margin, and/or whether a measured peak glucose level of the measured postprandial glycemic peak equals a predicted peak glucose level of the predicted postprandial glycemic peak given a glucose margin. Tolerance in the vicinity of the predicted peak is thus allowed to detect a good matching, hence confirming a two-hour postprandial "healthy" profile with glycemia<160 mg/dL, i.e. with no prolonged PP hyperglycemia.

In some embodiments, the glucose margin is at least +/−5% or +/−10% and at most +/−25%, preferably at least +/−15% and at most +/−20%, of the predicted or measured peak glucose level.

In some embodiments, the time margin is at least +/−5 min or +/−10 min and at most +/−25 min, preferably at least +/−15 min and at most +/−20 min.

The inventor has noticed satisfying hyperglycemia detection results (correspondence between good peak predictions and healthy profiles) for these margin values. For instance, peak matching with a glucose margin of +/−15% and a time margin of +/−20 min identifies about 85% of two-hour postprandial healthy profiles with glycemia<at least at 160 mg/dl while peak mismatching with the same margins identifies about 87% of two-hour postprandial hyperglycemia profiles.

In some embodiments, the measured peak glucose level and measured peak time respectively correspond to a local maximum blood glucose level measured during a postprandial time period and to the corresponding measure time. The postprandial time period may for instance be defined from the predicted peak time and the time margin (or more).

In some embodiments, the signal drives an insulin delivery device delivering insulin to the individual. Direct correction or adjustment of the insulin delivery (treatment) is taken without an intervention of the individual.

In some embodiments, the method further comprises obtaining a level of active insulin in the individual's blood and determining an insulin adjustment of an insulin delivery by the insulin delivery device based on the obtained active insulin level. The insulin adjustment may also be based on the measured peak glucose level. A personalized correction of the insulin delivery is thus obtained.

According to some features, the method further comprises temporarily adjusting a basal insulin delivery level and/or comprises setting a bolus insulin delivery level, based on the determined insulin adjustment. Of course, according to the level of insulin adjustment needed, only the basal level can be temporarily modified (e.g. if low insulin adjustment is required) or both basal temporary adjustment and bolus delivery can be done. A temporary adjustment typically lasts between 45 to 75 minutes, for example one hour. Alternatively, a sole bolus may be contemplated as insulin adjustment.

The above shows an automatized control of the insulin delivery device. Alternatively, the signal may include a display to the individual of a warning of risks (or not) of prolonged PPH, with e.g. the measured peak glucose level is displayed to drive the patient to take appropriate measures with respect to insulin delivery. The display may also indicate calculated temporary adjustment values for a basal insulin delivery and/or values for a bolus insulin delivery. The values may be based on known basal insulin delivery, measured or typed/input level of active insulin in the patient.

Another aspect of the invention relates to a non-transitory computer-readable medium storing a program which, when executed by a microprocessor or computer system in a device, causes the device to perform any method as defined above.

At least parts of the methods according to the invention may be computer implemented. Accordingly, the present invention may take the form of an entirely hardware embodiment, an entirely software embodiment (including firmware, resident software, micro-code, etc.) or an embodiment combining software and hardware aspects that may all generally be referred to herein as a "circuit", "module" or "system". Furthermore, the present invention may take the form of a computer program product embodied in any tangible medium of expression having computer usable program code embodied in the medium.

Since the present invention can be implemented in software, the present invention can be embodied as computer readable code for provision to a programmable apparatus on any suitable carrier medium. A tangible carrier medium may comprise a storage medium such as a hard disk drive, a magnetic tape device or a solid-state memory device and the like.

BRIEF DESCRIPTION OF THE FIGURES

Embodiments of the invention are now described, by way of example only, and with reference to the following drawings in which.

DETAILED DESCRIPTION

The present invention relates to assisting diabetic patients in early detecting risks of prolonged postprandial hyperglycemia, with a view of adjusting insulin delivery to drive two-hour postprandial glycemia down to PP glycemic recommendations (e.g. 160 mg/dL).

As apparent from the experiments below, the accuracy of the postprandial glycemic peak prediction is strongly correlated with a two-hour or less decrease of the postprandial glycemia below conventional recommendations, e.g. 160 mg/dL as prescribed by the International Diabetes federation. Based on this finding, coming postprandial hyperglycemia can be efficiently detected by merely checking the actual glycemic peak against the prediction.

Blood glucose levels of an individual can be continuously measured over time using a glucose sensor, from which values a measured postprandial glycemic peak is searched for. A predicted postprandial glycemic peak is also obtained. It is next checked whether the measured postprandial glycemic peak, if any, matches the predicted postprandial glycemic peak, i.e. whether it is close enough to the prediction. In case it does not match, prolonged postprandial hyperglycemia is detected and a corresponding signal can be emitted for example to adjust a delivery of insulin to the individual.

A new computer-aided prediction of postprandial glycemic peaks is also proposed. The inventor also found out that the slope or change rate of the postprandial glycemia and the total glycemia variation are strongly correlated through a linear relationship. Hence, simpler predictions of the postprandial glycemic peak can be achieved. Again, glucose level measurements of the individual having a meal can be obtained from a glucose sensor, including one pre-prandial blood glucose level measurement when the individual starts the meal. This defines the starting point of the post-meal glycemia rise. A postprandial glucose change rate is then determined from two blood glucose level measurements, two postprandial measurements or the pre-prandial one plus one postprandial measurement. Given the above finding, the postprandial glycemic peak, in particular the peak glucose level, can be linearly inferred (i.e. using the above-mentioned linear relationship) from the determined postprandial glucose change rate and from the pre-prandial blood glucose level measurement.

Figure 1:
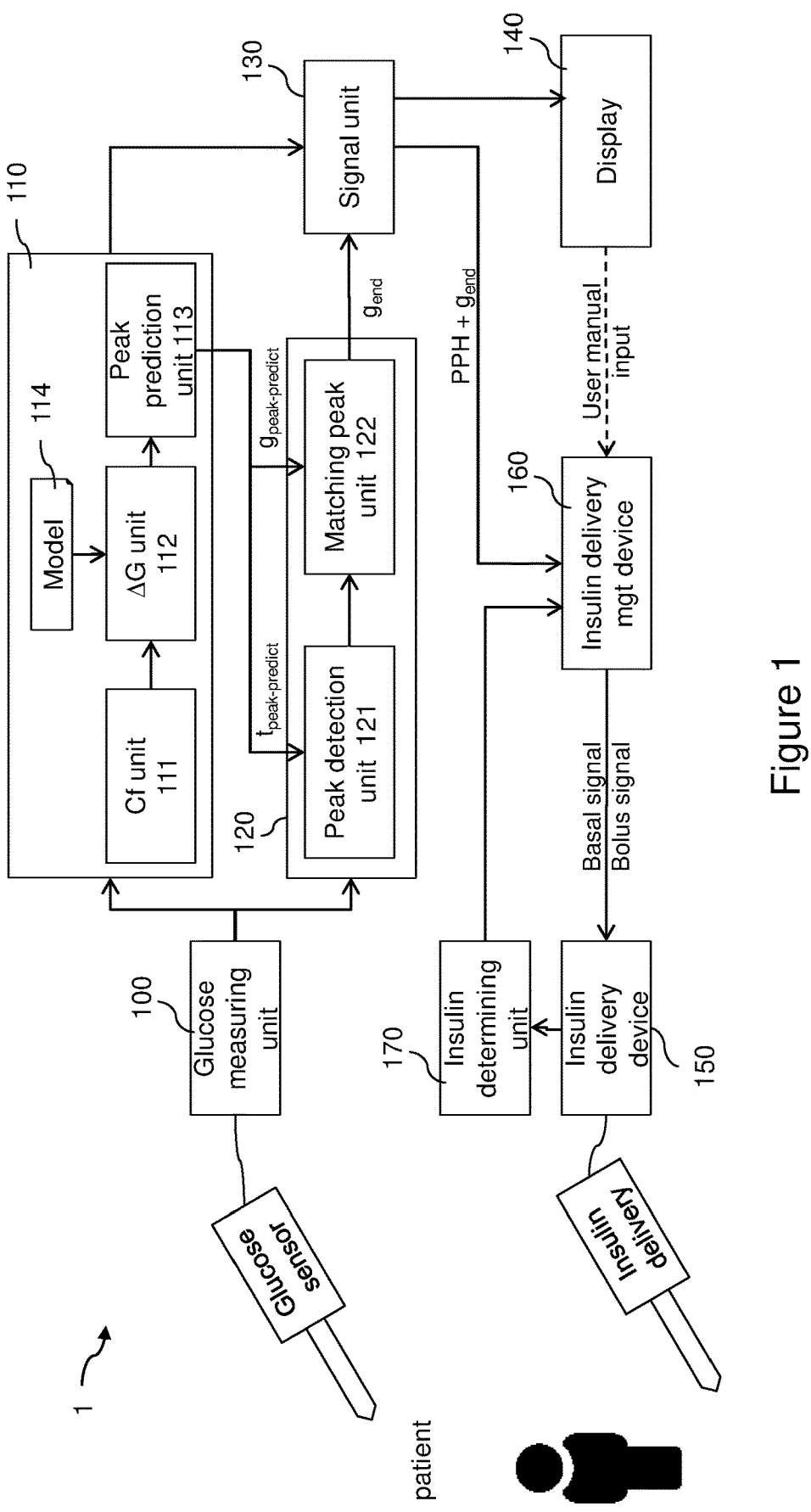
FIG. 1 illustrates an exemplary diabetes managing system for implementations of the invention.

FIG. 1 illustrates an exemplary system for implementations of the invention, in particular the prediction of a postprandial glycemic peak, the detection of prolonged postprandial hyperglycemia or not, and the control of insulin delivery, for example intradermic delivery.

The various units or devices of the system as described below preferably have synchronized clocks.

Diabetes managing system 1 comprises a glucose measuring unit 100 and a prediction unit 110.

Glucose measuring unit 100 is associated with one or more glucose sensors 105 to measure sugar level of an individual. Known sensors measure blood (or plasmatic) sugar level directly from the patient blood plasma. Other known sensors measure interstitial sugar level from which the equivalent blood sugar level can be inferred.

The glucose measuring unit 100 may be any continuous glucose monitoring system, CGMS, as known by one skilled in the art, equipped with a skin-contact or subcutaneous glucose sensor. CGMS may be associated with a mobile application that makes it possible to easily obtain the glucose level measurements and possibly to implement all or parts of the present invention. As an example, a CGM watch worn by the individual may be used.

A blood glucose level measurement is generally expressed in mg/dl (milligrams per deciliter of blood) associated with a measurement time (e.g. timestamp). Below, '$g_i$' refers to the blood glucose level value and '$t_i$' to the corresponding measurement time, hence forming the measurement ($g_i$, $t_i$).

A frequency of measuring blood glucose levels is generally from tens of seconds to few minutes.

Glucose measuring unit 100 may include a user interface or be connected to any user input device, in order to receive a user input indicating the coming or actual start of a meal taken by the individual. This information may be saved in memory as time information corresponding to the meal.

"Pre-prandial" means all that refers to the time period just before (i.e., less than 10 and preferably less than 5 minutes before) the meal time (i.e., time of food uptake by the individual) but also the few minutes after the start of the meal, usually less than 10 minutes, preferably less than 5 minutes. It corresponds to the period when the meal nutriments have not yet reached the blood. In embodiments, the user input advising the coming meal may correspond to the pre-prandial time $t_0$ to perform the pre-prandial glucose level measurement.

"Postprandial" refers to a time period after the pre-prandial period, usually a time period following the end of the meal. The individual may then input another user input to the glucose measure unit 100 to advise such meal end. Postprandial glucose level measurements may then take place afterwards.

The present invention seeks to detect prolonged postprandial hyperglycemia (PPH), usually two-hour PPH (i.e. hyperglycemia that lasts more than two hours after the meal time).

Prediction unit 110 receives blood glucose level measurements ($g_i$, $t_i$) from glucose measuring unit 100. It comprises a postprandial glycemia rate unit 111, a peak glucose increase unit 112 and a peak determination or prediction unit 113.

Postprandial glycemia rate unit 111 determines a postprandial glucose change rate Cf from two blood glucose level measurements. Indeed, the inventor noticed that the postprandial rise (before the peak) is roughly constant for a given meal and then the rise can be approximated by a mere slope for that meal.

Figures 2, 3, 4:
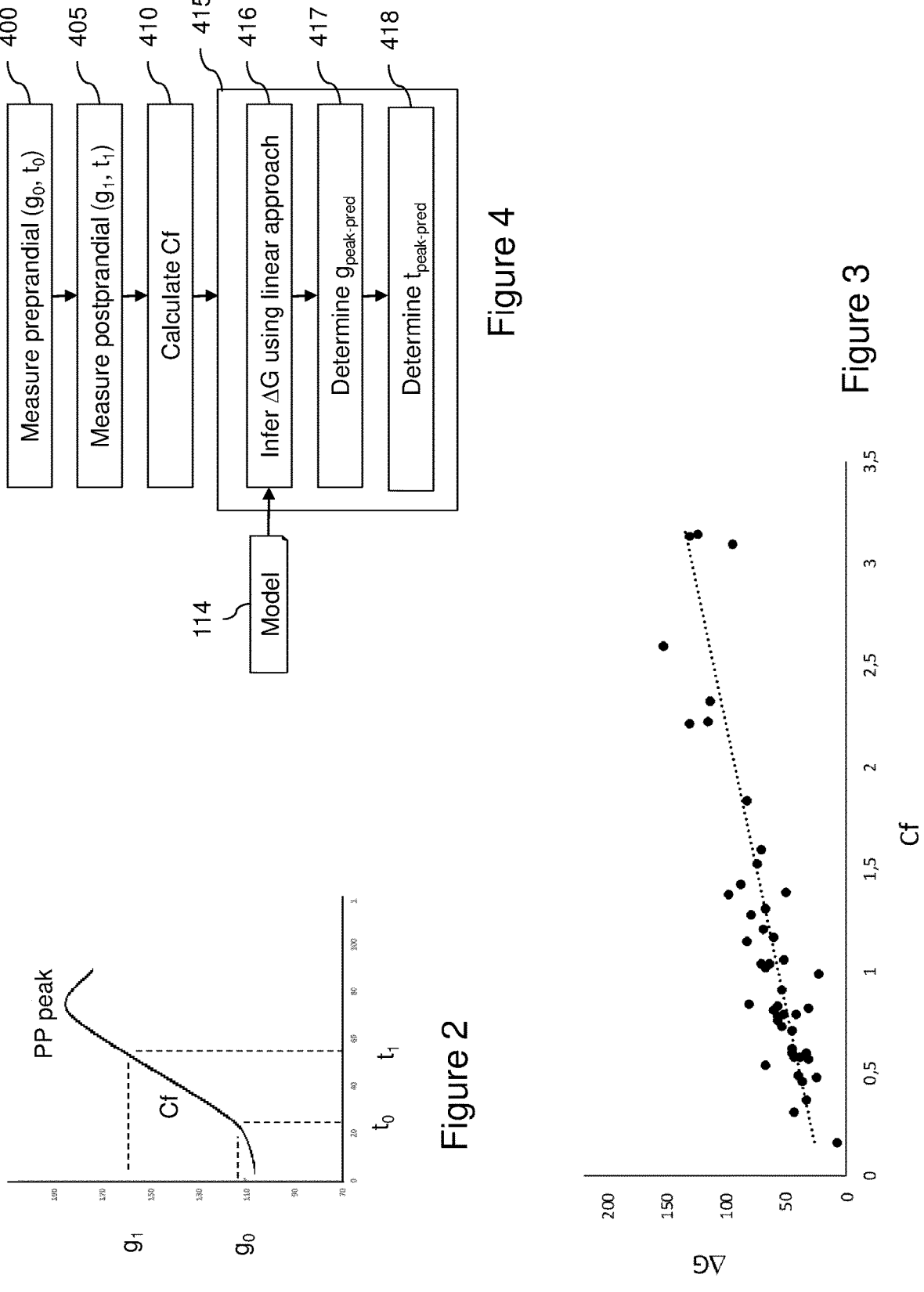
FIG. 2 illustrates a postprandial rise of glucose level.
FIG. 3 illustrates a linear relationship between peak glucose increase ΔG and glucose rise rate Cf.
FIG. 4 illustrates, using a flowchart, steps to obtain the predicted postprandial glycemic peak for a patient.

In one embodiment, the postprandial glucose change rate Cf is determined from a pre-prandial blood glucose level measurement ($g_0$, $t_0$) and one postprandial blood glucose level measurement ($g_1$, $t_1$) as illustrated in FIG. 2. In that case, prediction unit 110 can only receive one pre-prandial and one postprandial blood glucose level measurements from glucose measuring unit 100.

In another embodiment, the postprandial glucose change rate Cf is determined from two postprandial blood glucose level measurements ($g_1$ and $g_2$ at times $t_1$ and $t_2$). In that case, prediction unit 110 receives one pre-prandial ($g_0$, $t_0$) and two postprandial blood glucose level measurements from glucose measuring unit 100. The pre-prandial blood glucose level measurement ($g_0$, $t_0$) is further used by peak determination unit 113 as described below.

As mentioned above, the pre-prandial blood glucose level measurement ($g_0$, $t_0$) may be responsive to the user input advising a meal. The pre-prandial blood glucose level measurement ($g_0$, $t_0$) may correspond to the closest measurement made by glucose measuring unit 100 to the meal time (corresponding to the user input indicating a start of the meal) or the next one after the meal time. More generally, the pre-prandial blood glucose level measurement is made during the pre-prandial time period.

The postprandial blood glucose level measurement or measurements ($g_1$, $t_1$) ($g_2$, $t_2$) may be responsive to the user input advising a meal end. More generally, the postprandial blood glucose level measurements are made during the postprandial time period, a short time period after the meal time or the beginning of the blood glucose level rise, typically within 5 to 45 min after ending a meal, preferably 10-30 min, more preferably 10-20 min, even more preferably 10-15 min.

Preferably, the blood glucose level measurements used to determine the postprandial glucose change rate Cf are separated by at least 10 minutes, for instance by about 15 minutes.

Postprandial glycemia rate unit 111 thus calculates the postprandial glucose change rate Cf. For instance $Cf=(g_{last}-g_{first})/(t_{last}-t_{first})$ where $g_{first}$ is the blood glucose level measured at time $t_{first}$ (first measurement, either pre-prandial $[g_0, t_0]$ or postprandial $[g_1, t_1]$) and $g_{last}$ is the blood glucose level measured at time $t_{last}$ (second measurement, postprandial $[g_1, t_i]$ or $[g_2, t_2]$).

The change rate Cf is specific to a given meal, meaning that its value may be substantially different from one meal to the other, even for the same individual.

Peak glucose increase unit 112 and peak determination unit 113 next operate together to linearly infer a postprandial glycemic peak from the determined postprandial glucose change rate Cf and from the pre-prandial blood glucose level measurement $(g_0, t_0)$.

The peak is defined by a peak glucose level and a peak time, representing the time instant at which the peak glucose level occurs. The peak glucose level $(g_{peak-pred})$ is predicted from rate Cf thanks to a linear relationship. The peak time $(t_{peak-pred})$ is then predicted, still using a linear approach since the glucose level rise is modeled as a line $(g_i=Cf\cdot t_i+g_0)$.

In embodiments, peak glucose increase unit 112 receives the postprandial glucose change rate Cf as input and outputs a predicted peak glucose increase $\Delta G_{pred}$. The increase $\Delta G_{pred}$ represents the predicted magnitude of the glucose increase for the individual following the meal uptake.

One finding from the inventor is that rate Cf and peak increase $\Delta G$ are linked one to the other through a linear relationship. This linear relationship may be stored in memory 114 as a linear function or as a lookup table.

The linear relationship may be learnt from learning data. The learning data may be specific to the individual, in which case the linear relationship is individualized. Alternatively, the inventor shows below (experiments) that the learning data may not be specific to the individual, hence mixing data from various individuals (including or not the monitored individual). The same linear relationship can then be used for plural individuals.

The learning data can be formed from measured glycemia profiles of the individual or individuals over time, as plural sets of measured peak increases $\Delta G_{measured}$ and corresponding (average) slope Cf of the curve rise of the profiles.

A mere linear regression is then used from the learning data to known the linear relationship between Cf and $\Delta G_{measured}$. FIG. 3 illustrates an exemplary linear relationship between $\Delta G$ and Cf obtained through linear regression of learning data (the dots).

Peak glucose increase unit 112 thus infers peak increase $\Delta G_{pred}$ from input measured rate Cf by merely reading the look-up table or calculating it from the linear function 114.

Predicted peak increase $\Delta G_{pred}$ is next input to peak determination unit 113 which outputs the predicted postprandial glycemic peak $(g_{peak-pred}, t_{peak-pred})$ from the pre-prandial blood glucose level measurement $(g_0, t_0)$.

Typically, $g_{peak-pred}=g_0+\Delta G_{pred}$ and $t_{peak-pred}=t_0+\Delta G_{pred}/Cf$.

A predicted postprandial glycemic profile can then be defined as being made of $(g_0, t_0)$, a line with slope Cf, a maximum at $(g_{peak-pred}, t_{peak-pred})$ and then a decrease. As an illustration, the decrease may be defined using a predefined glucose level (e.g. 120 or 140 or 160 mg/dL), two hours (120 min) or the like after the meal or the pre-prandial measurement.

FIG. 4 illustrates, using a flowchart, steps to obtain the predicted postprandial glycemic peak $(g_{peak-pred}, t_{peak-pred})$ for an individual.

At step 400, the pre-prandial blood glucose level measurement $(g_0, t_0)$ is obtained from glucose measuring unit 100. It is for instance a measurement made when the user signals the start of a meal.

At step 405, a postprandial blood glucose level measurement $(g_1, t_1)$ is obtained, for instance 15 min after the pre-prandial measurement. In a variant, two postprandial blood glucose level measurements $(g_1, t_1)$ $(g_2, t_2)$ are obtained where $t_2-t_1$ is at least 10 min, for instance 15 min, and $t_1$ is a few minutes (less than 5 minutes for example) after the end of the meal.

At step 410, the postprandial glucose change rate Cf is obtained by postprandial glycemia rate unit 111 from two measurements obtained at steps 400 and 405.

Next, at step 415, a postprandial glycemic peak is predicted for the individual from Cf, using a linear approach.

Step 415 comprises substep 416 where peak glucose increase unit 112 infers peak increase $\Delta G_{pred}$ from Cf, using look-up table or linear function 114; substep 417 where peak determination unit 113 determines the predicted peak glucose value of the predicted postprandial glycemic peak: $g_{peak-pred}=g_0+\Delta G_{pred}$ and, substep 418 where peak determination unit 113 determines the predicted peak time of the predicted postprandial glycemic peak: $t_{peak-pred}=t_0+\Delta G_{pred}/Cf$.

The predicted postprandial glycemic peak can then be used in a method for assisting a diabetic individual, in particular for helping the individual to anticipate prolonged postprandial hyperglycemia and then anticipate insulin delivery corrections. This is described now. In a variant, this assisting method may rely on any other method for predicting the PP glycemic peak.

Back to FIG. 1, to achieve this goal, diabetes managing system 1 also includes a matching peak determination unit 120 and a signal emitting unit 130.

Matching peak determination unit 120 receives continuous postprandial blood glucose level measurements $(g_i, t_i)$ from glucose measuring unit 100 and is configured with the predicted postprandial glycemic peak $(g_{peak-pred}, t_{peak-pred})$. Based on these data, it determines whether the blood glucose level measurements $(g_i, t_i)$ include a measured postprandial glycemic peak matching the predicted postprandial glycemic peak.

To do so, matching peak determination unit 120 includes peak detection subunit 121 and matching peak value subunit 122.

Peak detection subunit 121 checks whether the actual postprandial glycemic peak occurs during a peak monitoring window defined around the predicted peak time $t_{peak-pred}$. Indeed, it is assumed that a real peak occurring too early or too late with respect to the peak time does not match the predicted postprandial glycemic peak. Peak detection subunit 121 is thus configured by predicted peak time $t_{peak-pred}$ together with a preset time margin. In embodiments, the time margin is at least +/−5 min or +/−10 min and at most +/−25 min, preferably at least +/−15 min and at most +/−20 min. For instance, it is +/−15 min or +/−20 min. This finally defines a monitoring time window from $t_{peak-pred}$-margin to $t_{peak-pred}$+margin. This advantageously limits the time processing (peak search) to this time window.

Peak detection subunit 121 receives the continuously-measured postprandial profile of the individual made of the blood glucose level measurements $(g_i, t_i)$. Subunit 121 searches for a local maximum in the profile. This may be made by searching a zero in the derivative of the profile curve within the monitoring time window, or merely by looking for when the blood glucose level starts decreasing after an initial rise.

It may happen that no peak is determined by subunit 121 for instance if the postprandial glycemic profile still rises at the end of the monitoring time window.

When a peak is determined, its characteristics are saved, namely the peak time $t_{peak-measure}$ and the corresponding blood glucose level $g_{peak-measure}$. The measured peak glucose level and measured peak time respectively correspond to a local maximum blood glucose level measured during a postprandial time period and to the corresponding time of measure.

Matching peak value subunit 122 receives either the indication of no detected peak with the last blood glucose level $g_{end}$ measured during the monitoring time window (case 1) or the peak blood glucose level $g_{peak-measure}$ (case 2). Matching peak value subunit 122 is configured by predicted peak glucose level $g_{peak-pred}$ together with a preset glucose margin. In embodiments, the glucose margin is at least +/−5% or +/−10% and at most +/−25%, preferably at least +/−15% and at most +/−20%, of the predicted or measured peak glucose level. For instance, it is +/−15% or +/−20%. This value finally defines a glucose level window from $g_{peak-pred}$-margin to $g_{peak-pred}$+margin.

In both cases, matching peak value subunit 122 outputs whether the postprandial profile curve includes a peak matching the predicted peak, i.e. a peak whose characteristics meet the monitoring time window and the glucose level window.

For case 1, matching peak value subunit 122 directly outputs a lack of matching peak (peak mismatch) with the $g_{end}$ value.

For case 2, matching peak value subunit 122 checks whether the received peak blood glucose level $g_{peak-measure}$ falls within the glucose level window, i.e. whether:

$$g_{peak-pred}\text{-margin}<g_{peak-measure}<g_{peak-pred}\text{+margin}.$$

In the affirmative, a matching peak is found, and subunit 122 outputs a signal indicative of peak match together with the last blood glucose level $g_{end}$ measured during the monitoring time window.

In the negative, the detected peak does not match the predicted peak. In that case, subunit 122 outputs a signal indicative of peak mismatch, together with $g_{end}$.

The output of subunit 122 is provided as input to signal emitting unit 130. The latter uses the input to issue a signal of prolonged postprandial hyperglycemia risk in case of negative determining by matching peak value subunit 122, and possibly a signal of absence of prolonged postprandial hyperglycemia risk in case of positive determining.

Indeed, as mentioned above, the inventor has found that a correct postprandial glycemic peak prediction is strongly correlated with a two-hour or less decrease of the postprandial glycemia below conventional recommendations (healthy profile), and an incorrect peak prediction is strongly correlated with a postprandial hyperglycemia profile (prolonged PP hyperglycemia that lasts more than conventional 2 hours). Hence, peak mismatch as output by matching peak value subunit 122 indicates a postprandial hyperglycemia profile.

The signal may be a mere indication to the individual, for instance an indication displayed on a screen 140. The display may also include corrective measures to be taken by the individual for example with respect to a modification of the insulin delivery as described below, and/or include value $g_{end}$ (from which the correction should be calculated).

The signal may also be a control signal to drive an insulin delivery device 150 as described below.

Figures 5, 6, 7:
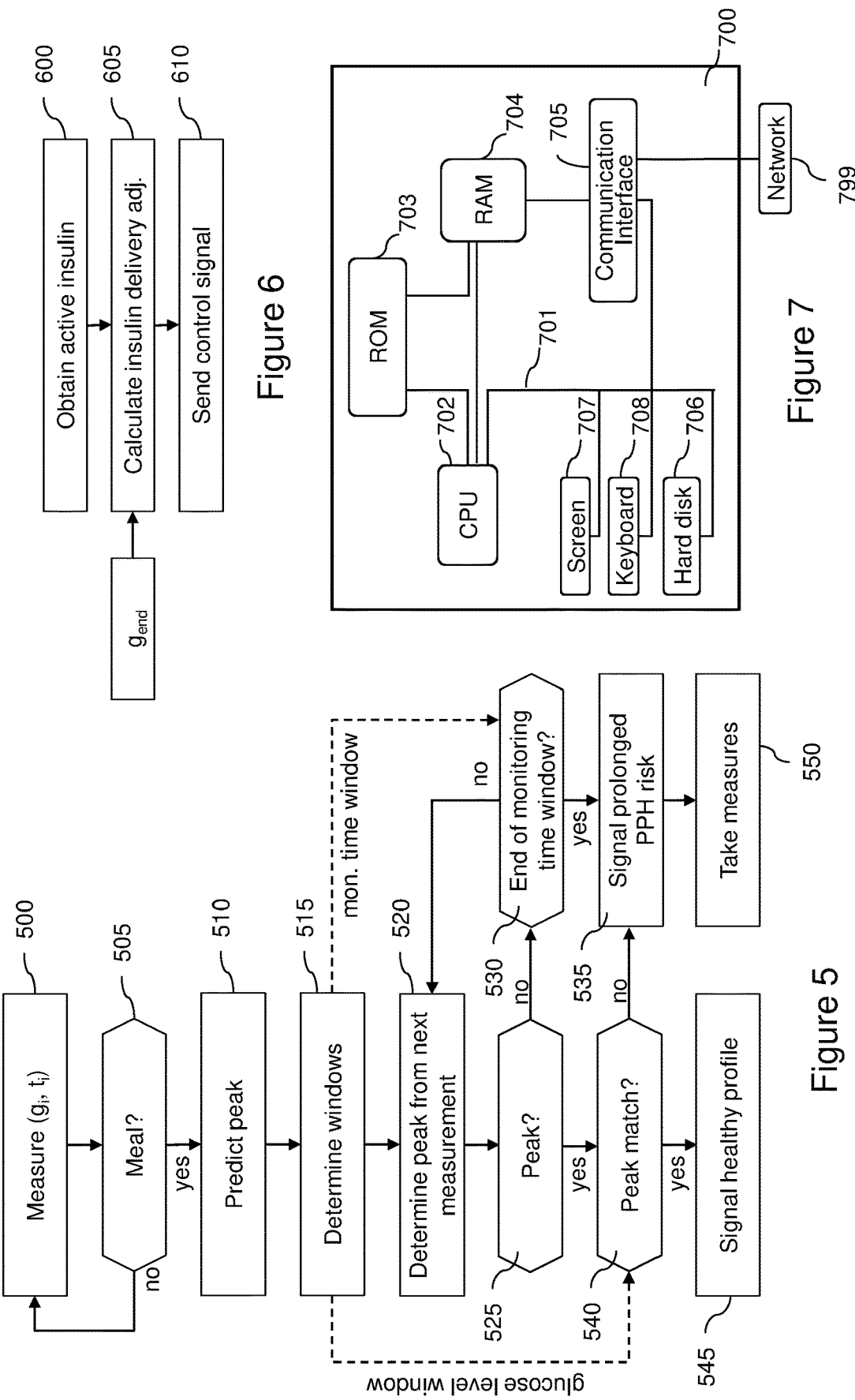
FIG. 5 illustrates, using a flowchart, steps to assist the patient in detecting postprandial hyperglycemia (PPH)
FIG. 6 illustrates, using a flowchart, steps to adjust insulin delivery to a patient based on a detected postprandial hyperglycemia (PPH)
FIG. 7 schematically illustrates a computer device managing the diabetes managing system.

FIG. 5 illustrates, using a flowchart, steps to assist the individual in detecting prolonged postprandial hyperglycemia (PPH) risks.

Postprandial blood glucose levels ($g_i$, $t_i$) are continuously obtained at step 500 by glucose measuring unit 100.

The next steps to determine prolonged PPH risks may be triggered by a user input indicating a meal (test 505).

Step 510 consists in predicting a postprandial glycemic peak ($g_{peak-pred}$, $t_{peak-pred}$) of the individual based on some measurements. This may involve prediction unit 110 and implement the steps of FIG. 4. In variant, other PP peak prediction methods can be used.

From this step, the monitoring time window and the glucose level window can be calculated at step 515 as described above.

At step 520, the continuous postprandial blood glucose level measurements ($g_i$, $t_i$) are analyzed by peak detection subunit 121 in order to find a peak.

As the measurements are successively processed, it is determined whether a local maximum (peak) is present (test 525), for instance by comparison to previous measurements. Filtering may be implemented to average successive measurements before searching for a local maximum, in order to avoid detecting a local maximum due to occasional measurement errors.

If no peak is detected at test 525, it is checked whether the monitoring time window ends (test 530). In the affirmative, a peak mismatch signal is sent to signal emitting unit 130 and the process continues at step 535. In the negative, the next measurement is processed by looping back to step 520.

If a peak is detected at test 525, matching peak value subunit 122 checks at step 540 whether the peak meets the glucose level window requirement, i.e. whether $g_{peak-pred}$-margin≤$g_{peak-measure}$≤$g_{peak-pred}$+margin. In the affirmative, a peak match signal is sent to signal emitting unit 130 and the process continues at step 545 where unit 130 emits a signal indicating a healthy profile, i.e. with low risk of prolonged postprandial hyperglycemia. In the negative of test 540, a peak mismatch signal is sent to signal emitting unit 130 and the process continues at step 535.

At step 535, unit 130 emits a prolonged PPH risk signal to the individual (through display on screen 140) or to insulin delivery managing device 160 driving the insulin delivery device 150. The prolonged PPH risk signal indicates a prolonged postprandial hyperglycemia is about to occur for the individual. Such signal aims at triggering insulin corrective measures at step 550.

The PPH risk signal may include values $g_{end}$ corresponding to the blood glucose level at the end of the monitoring time window, or to any subsequent other blood glucose level measured before the next steps are performed.

Back to FIG. 1, diabetes managing system 1 thus also includes insulin delivery managing device 160, insulin delivery device 150 and an insulin determining unit 170.

Insulin delivery managing device 160 is connected to both insulin determining unit 170 to obtain a level of active insulin in the individual's blood and to insulin delivery device 150 to control the actual delivery of insulin to the individual based on the measured active insulin level and the measured peak in case of detected PPH risk.

Insulin active is the amount of insulin already administered and not cleared by the organism.

Insulin delivery managing device 160 may thus receive, as input, prolonged PPH risk signal from signal emitting unit 130. In a variant, the individual may manually provide insulin delivery managing device 160 with a prolonged PPH indication together with value $g_{end}$ (for instance obtained from screen 140).

Insulin delivery managing device 160 may be built within the same device as units 100, 110, 120 and 130, meaning the diabetes managing system 1 is one and the same device with some sensors. Alternatively, units 100, 110, 120 and 130 may form a first device and units 150, 160, 170 may form a second device, connected or not to the first device to receive signals from unit 130.

Insulin delivery managing device 160 may be embodied in an electromechanical insulin pump.

Insulin determining unit 170 is a computing (hardware and/or software) unit that may be autonomous or embedded in insulin delivery managing device 160 or insulin delivery device 150. It receives, from insulin delivery device 150, the history of insulin delivery from which it infers the current level of insulin still active in the individual's body. Various formulae describing the decrease of insulin in bodies next to its delivery are known by the skilled person. Hence, they are not further detailed. Insulin determining unit 170 thus obtains a level of active insulin in the individual's blood, for example responsive to receiving the prolonged PPH risk signal from unit 130 (directly or through unit 160) or a user input.

The obtained level of active insulin is provided to insulin delivery managing device 160 together with the prolonged PPH risk signal. Insulin delivery managing device 160 determines an insulin adjustment of an insulin delivery by insulin delivery device 150 based on the obtained active insulin level and $g_{end}$.

Insulin adjustments or corrections may be estimated based on a glucose level target value, e.g. 120 or 140 mg/dL. According to literature, an arbitrary value of 1.5 unit of insulin is proposed to decrease glycemic values by 30 mg/dL. Of course, this value (30 mg/dL) is highly dependent from one individual to the other. Hence, an individual value specific to the individual concerned (for example learned from medical investigation on the individual) may be used.

The amount of insulin needed can thus be calculated from $g_{end}$ (to reach 120 mg/dL) and be compared to the amount of insulin still active as obtained from unit 170, noted $I_{active}$. For example, $(g_{end}-120)/30$ gives the amount $I_{needed}$ of units of insulin needed to prevent from the prolonged PPH.

If the amount of the total insulin needed is superior to the amount of active insulin, an insulin delivery to the individual can be made, usually a continuous insulin delivery is adjusted.

For example, if $I_{needed}>I_{active}$, a correction of $I_{needed}-I_{active}$ units of insulin can be provided. If $I_{needed}\leq I_{active}$, no correction is made.

The insulin delivery adjustment may comprise temporarily adjusting a basal insulin delivery level and/or setting a bolus insulin delivery level. For instance, an increase of the basal value is made in priority when possible for one hour (or another duration, between 30 min and two hours) given a predefined total basal limit (for example a total basal limit of two units/hour). The remaining part of the correction is made as an insulin bolus ($I_{needed}-I_{active}$ minus the basal-based correction).

Therefore, insulin delivery managing device 160 calculates the basal-based insulin adjustment and the bolus insulin correction, and sends a corresponding signal to insulin delivery device 150. The latter immediately adjusts the basal insulin delivery based on the basal-based insulin adjustment (e.g. for one hour) and proceeds with an additional bolus of insulin based on the bolus insulin correction.

The insulin adjustment is made early in the detection of the prolonged PPH, hence substantially reducing risks of prolonged PP hyperglycemia.

FIG. 6 illustrates, using a flowchart, steps to adjust insulin delivery to the individual based on the detected prolonged postprandial hyperglycemia (PPH). The process starts when a prolonged PPH risk signal is received from unit 130 or corresponding information is input by the individual in insulin delivery managing device 160.

At step 600, insulin delivery managing device 160 obtains a level of active insulin in the individual's blood from insulin determining unit 170.

At step 605, insulin delivery managing device 160 calculates the insulin delivery adjustment as described above using $g_{end}$. A basal-based insulin adjustment and/or a bolus insulin correction are computed.

At step 610, a corresponding signal is sent to insulin delivery device 150 thereby controlling the actual delivery of insulin to the individual according to the basal-based insulin adjustment and/or the bolus insulin correction.

The invention as exemplified in the embodiments above allows a diabetic individual, in particular an insulin-dependent individual suffering from T1D, to quickly anticipate the evolution of its glycemia, to anticipate prolonged postprandial hyperglycemia and have personalized corrective recommendations for a rapid return to normalized blood sugar levels.

FIG. 7 schematically illustrates a computer device 700 managing the diabetes managing system 1. Computer device 700 may for instance implement prediction unit 110, matching peak determination unit 120, signal emitting unit 130, insulin delivery managing device 160 and include or be connected to one or more of the measuring and delivering units 100, 150, 170. Where several devices are used in system 1, several computer devices 700 may be used.

Computer device 700 is configured to implement at least one embodiment of the present invention. Computer device 700 may preferably be a device such as a micro-computer, a workstation or a light portable device. Computer device 700 comprises a communication bus 701 to which there are preferably connected:

a central processing unit 702, such as a microprocessor, denoted CPU;

a read only memory 703, denoted ROM, for storing computer programs for implementing the invention;

a random-access memory 704, denoted RAM, for storing the executable code of methods according to embodiments of the invention as well as the registers adapted to record variables and parameters necessary for implementing methods according to embodiments of the invention;

a communication interface 705 connected to a network 799 in order to communication with a user or operator device and/or with other devices/units of system 1, for instance the measuring and delivering units 100, 150, 170; and a data storage means 706 such as a hard disk or a flash memory, for storing computer programs for implementing methods according to one or more embodiments of the invention as well as any data necessary for embodiments of the invention, including inter alia model 114.

Optionally, computer device 700 may also include a screen 707 serving as a graphical interface with an operator, for instance to configure the system by means of a keyboard

708 or any other pointing means and/or to display the results of the prediction process or of the PPH detection (e.g. display screen 140), for instance to display the PPH signal and measured peak glucose level $g_{peak\text{-}measure}$.

Computer device 700 may be optionally connected to various peripherals useless for the present invention, each being connected to an input/output card (not shown).

Preferably the communication bus provides communication and interoperability between the various elements included in the computer device 700 or connected to it. The representation of the bus is not limitative and in particular the central processing unit is operable to communicate instructions to any element of the computer device 700 directly or by means of another element of the computer device 700.

Exclusion criteria: (1) patient with no continuous glucose monitoring system, CGMS; (2) condition(s) other than diabetes compromising the safety of the patient (bulimia, anorexia, . . . ); (3) patient undergoing dialysis; (4) patient with known alcohol or drug dependency or abuse.

The selected patients were informed about the study and accepted the protocol in confidence with the investigator. Patients were diagnosed with type 1 diabetes. Before being enrolled in the study, each patient underwent a thorough review of their medical history (i.e., years since diagnosis, diabetes complications, HbA1c level), as summarized in the following table. "P" stands for patient identifier, "G" for gender, "A" for age in years, "DA" for diabetes age in years, "ODC" for others diabetic complications.

TABLE 1

| | | | | | patient characteristic at baseline | | | |
| P | G | A | DA | ODC | HbA1c (%) | CGMS used | Insulin brand | Insulin deliv. device |
|---|---|---|---|---|---|---|---|---|
| 1 | F | 17 | 2 | None | 6.7-7.5 | FreeStyle | Humalog ® (Lilly ®) | Pump (Omnipod) |
| 2 | M | 45 | 4 | None | 6.9-7.5 | FreeStyle | FIASP ® (NovoNordisk ®) | Pump (Omnipod) |

The executable code may optionally be stored either in read only memory 703, on the hard disk 706 or on a removable digital medium (not shown). According to an optional variant, the executable code of the programs can be received by means of the communication network 799, via the interface 705, in order to be stored in one of the storage means of the computer device 700, such as the hard disk 706, before being executed.

The central processing unit 702 is preferably adapted to control and direct the execution of the instructions or portions of software code of the program or programs according to the invention, which instructions are stored in one of the aforementioned storage means. On powering up, the program or programs that are stored in a non-volatile memory, for example on the hard disk 706 or in the read only memory 703, are transferred into the random-access memory 704, which then contains the executable code of the program or programs, as well as registers for storing the variables and parameters necessary for implementing the invention.

EXPERIMENTAL RESULTS

Scope of the Experiments

The purpose of the experiments was to investigate the efficiency of the proposed peak prediction in the process of anticipating postprandial hyperglycemia.

Experiment 1

Protocol—Selected Patients

Case studies were conducted between June 2020 and January 2021. Patients were selected at the discretion of the investigator according to the following inclusion/exclusion criteria:

Inclusion criteria: (1) 16-year-old or older man or woman; (2) patient with documented and stable type 1 diabetes with reasonable metabolic control at least every four months (Hemoglobin A1c levels<12%).

In short, patient 1 was a 17-year-old woman with type 1 diabetes (HbA1c level comprised between 6.7% and 7.5%) diagnosed two years before the study. No other diabetic complications were reported during the study. Details of insulin brand and CGMS used are reported in the table above. Basal insulin level administered increased from 20 units/day to 40 units daily during the study period.

Patient 2 was a 45-year-old man with type 1 diabetes (HbA1c level comprised between 6.9% and 7.5%) diagnosed four years before the study. No other diabetic complications were reported during the study. Details of insulin brand and CGMS used are reported in the table above. Basal insulin level during the study were 10-15 units a day.

Protocol—Study

The study was divided into two subparts based on data to be assessed.

First subpart concerned the accuracy of the prediction of the postprandial (PP) peak, i.e. of the determination of both PP peak glucose and time values. For this, both blood glycemic values (i.e. glucose levels) were measured using continuous glucose monitoring system (CGMS) at the beginning of a complex meal and then 10-15 min after the end. Associated measuring times were recorded. These values were entered into the algorithm and a prediction of both PP peak glucose and time values ($g_{peak\text{-}pred}$, $t_{peak\text{-}pred}$) was calculated.

Second subpart checked the assumption that a strong correlation exists between the PP glucose profile and the accuracy of the PP peak prediction. PP glucose profiles, including real values for the PP peak, were extracted from data collected by the associated CGMS.

Finally, the algorithm was used to anticipate risks of prolonged PP hyperglycemia (i.e. more than two hours) and then implement insulin delivery correction.

Results and Discussion—Predictive Algorithm for PP Peaks

Glucose level measurements were continuously made by the CGMS from which the glucose increase $\Delta G$ of the postprandial peak was determined. Glucose increase $\Delta G$ corresponds to the difference between PP peak glycemic value (i.e. maximum glucose level) and the pre-prandial glycemic value measured just before starting the meal.

133 PP glucose profiles (i.e. 133 meals) were obtained for patient 1 and 42 PP glucose profiles were obtained for patient 2. FIG. 2 schematically illustrates such a PP glucose profile were a PP peak is clearly visible.

Figure 8:
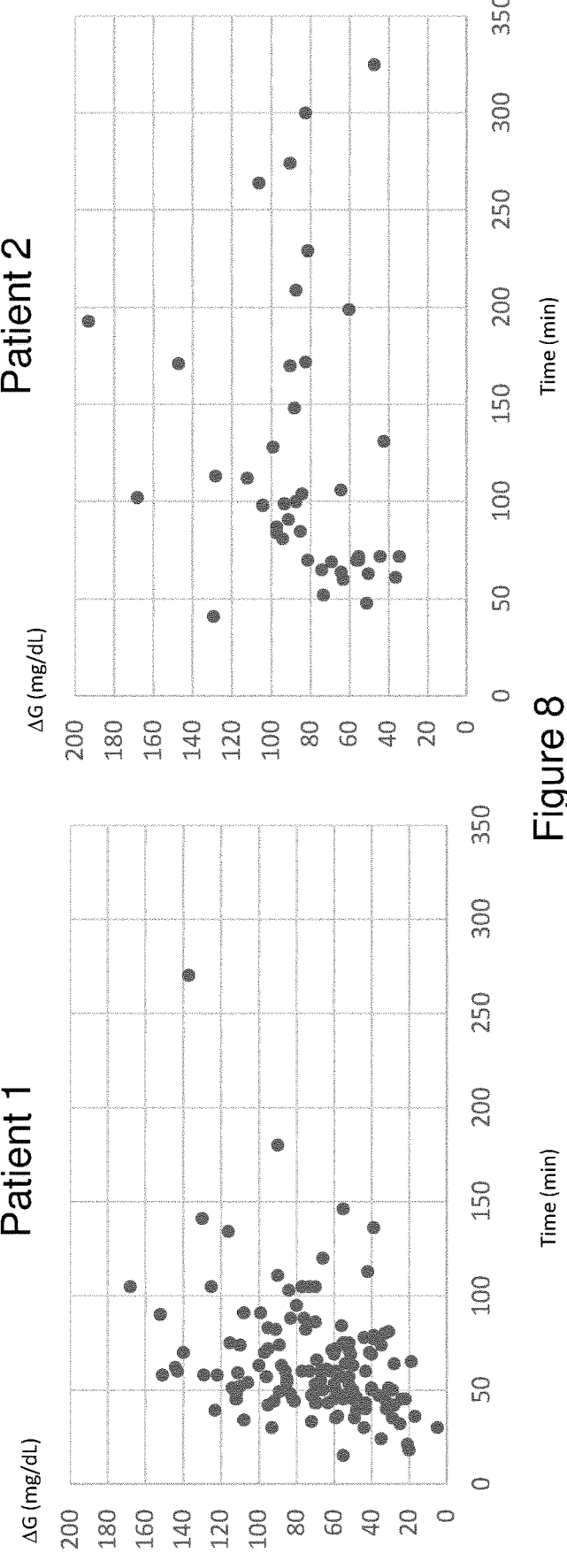
FIG. 8 illustrates postprandial glucose dynamics by depicting PP peak glucose increase ΔG as a function of the number of minutes needed to reach the PP peaks.

FIG. 8 illustrates the postprandial dynamics, i.e. depicts the PP glucose increase $\Delta G$ as a function of the number of minutes needed to reach the PP peaks from the start of the meal, for patients 1 and 2.

The Figure shows a high variable PP glycemic increase $\Delta G$ for patient 1 (left plot) with the PP peak generally reached in less than 100 minutes.

Less variability in postprandial glycemic increase $\Delta G$ was observed for patient 2 (right plot), but with a higher variability in the time needed to reach the PP peak, often superior to 150 minutes.

Although PP peak profiles are extremely variable, the quick rise in blood glucose levels of a healthy profile can be characterized as a linear equation between blood glucose level and time as shown in FIG. 2. A regression coefficient line Cf can be determined.

Assuming the International Diabetes Federation's recommendation to have a decreased glucose level below 160 mg/dL within two hours, the measured PP glucose profiles of patients 1 and 2 were classified into PP hyperglycemia (PPH) profiles (not meeting the above recommendation, i.e. showing a prolonged PPH superior beyond two hours) and PP healthy profiles (meeting the recommendation).

The following table summarizes this classification by counting up the PP healthy profiles from 43 profiles (out of the 133) of Patient 1 and the 42 profiles of Patient 2.

TABLE 2

| PPH profiles | | | |
|---|---|---|---|
| | n | Patient 1 | Patient 2 |
| # of meals | 85 | 43 | 42 |
| # healthy profiles | 39 | 25 | 14 |
| % | 46% | 58% | 33% |

As shown in the table, only 46% of the measured profiles did reach the recommended medical values (58% for patient 1 and 33% for patient 2, respectively).

The distribution of slope Cf has thus be separately analyzed for the PPH profiles and the healthy profiles.

Figures 9, 9A:
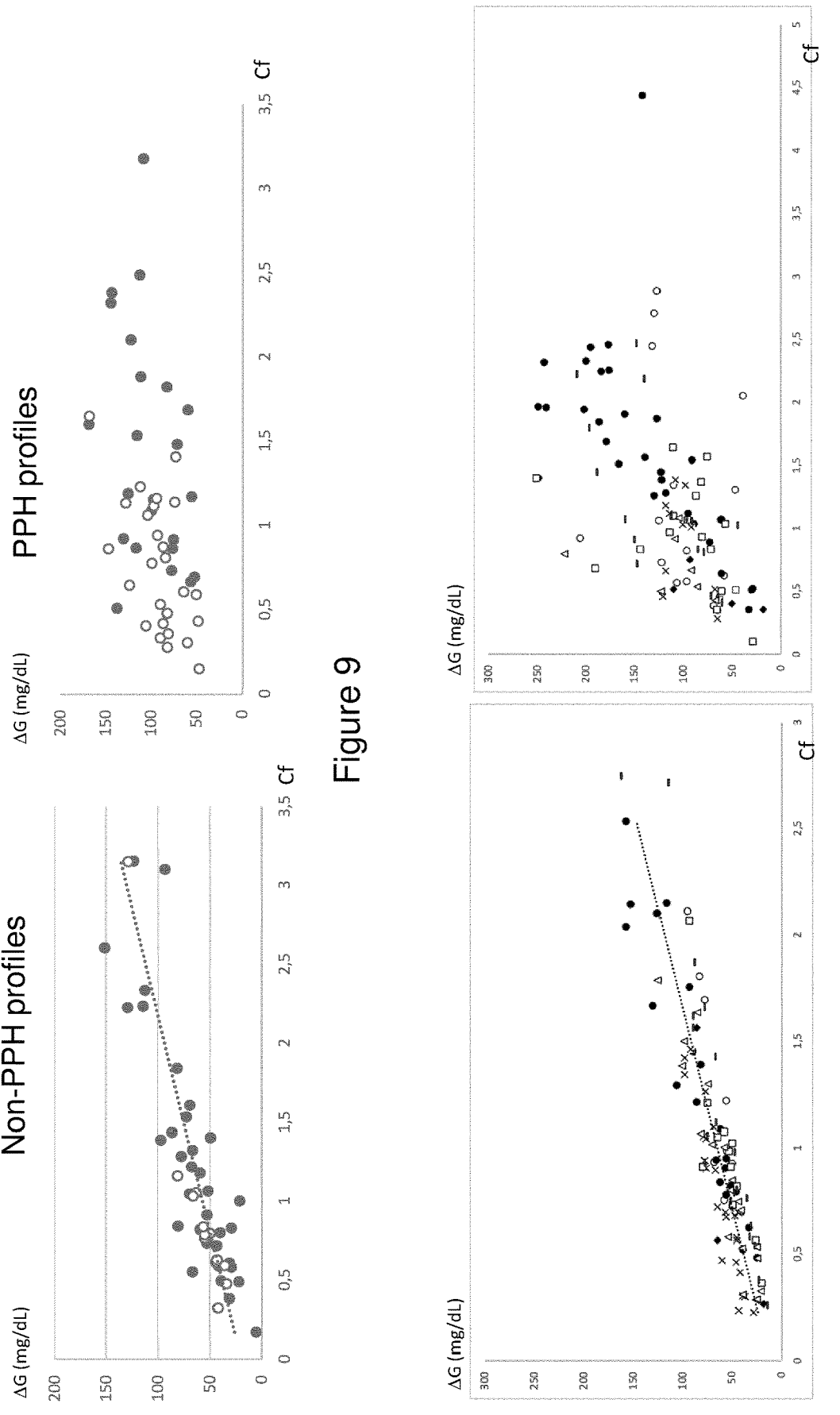
FIG. 9 illustrates the distribution of rise rate Cf as a function of the PP peak glycemic increase ΔG according to first experiment data.
FIG. 9a illustrates the distribution of the PP peak glycemic increase ΔG as a function of rise rate Cf according to second experiment data.

FIG. 9 illustrates the distribution of the PP glycemic increase $\Delta G$ as a function of slope Cf for the two patients (plain dots for patient 1 and clear dots for patient 2). The plot on the left side corresponds to the distribution for healthy profiles only, while the plot on the right side corresponds to the distribution for PPH profiles only.

Interestingly, the healthy profiles (left side) show a linear relationship between $\Delta G$ and Cf ($r^2=0.8$) while no linear relationship ($r^2=0.2$) has been identified with the PPH profiles.

This linearity between $\Delta G$ and Cf is of particular importance as Cf can easily be calculated using two blood glucose level measurements and then $\Delta G$ can easily be obtained using the linear relationship. Hence, the PP peak can be predicted in few steps. This is explained above with respect to FIG. 4.

The linear relationship between $\Delta G$ and Cf was calculated using linear regression on an initial subset of measurements from Patient 1. The initial subset was made of the healthy profiles from the 133-43 profiles mentioned above (which were the first measurements obtained).

The other measurements were used to validate the prediction accuracy, while improving the linear relationship (the linear regression was repeatedly calculated again as each new measurement).

The table below reports the accuracy of the peek prediction in terms of peak glucose level (shown through $\Delta G$=glucose peak-$g_0$) and peak time (shown through $\Delta t$=peak time-$t_0$), for 39 healthy profiles.

TABLE 3

| peak prediction accuracy | | | |
|---|---|---|---|
| Mean $\Delta G$ | $-1.94 \pm 9.28\%$ | Mean $\Delta t$ | $2 \pm 16.38$ min |
| $\Delta G < [\pm 20\%]$ | 95% | $\Delta t < [\pm 20$ min$]$ | 95% |
| $\Delta G < [\pm 15\%]$ | 87% | $\Delta t < [\pm 15$ min$]$ | 90% |
| $\Delta G < [\pm 10\%]$ | 77% | $\Delta t < [\pm 10$ min$]$ | 74% |
| $\Delta G < [\pm 5\%]$ | 54% | $\Delta t < [\pm 5$ min$]$ | 67% |
| $\Delta G < [\pm 20\%]$ & $\Delta t < [\pm 20$ min$]$ | | 90% | |
| $\Delta G < [\pm 20\%]$ & $\Delta t < [\pm 15$ min$]$ | | 87% | |
| $\Delta G < [\pm 20\%]$ & $\Delta t < [\pm 10$ min$]$ | | 72% | |
| $\Delta G < [\pm 15\%]$ & $\Delta t < [\pm 20$ min$]$ | | 85% | |
| $\Delta G < [\pm 15\%]$ & $\Delta t < [\pm 15$ min$]$ | | 82% | |
| $\Delta G < [\pm 15\%]$ & $\Delta t < [\pm 10$ min$]$ | | 67% | |
| $\Delta G < [\pm 10\%]$ & $\Delta t < [\pm 20$ min$]$ | | 74% | |

As shown in the table, 87% of the measured PP peak glycemic blood values ($g_{peak-measure}$) matched the corresponding predicted ones ($g_{peak-pred}$) within a range of $\Delta G \pm 15\%$. Prediction accuracy reached up to 95% within a glucose level margin of $\pm 20\%$.

With respect to the peak time, 90% of the measured PP peak times ($t_{peak-measure}$) matched the corresponding predicted ones ($t_{peak-pred}$) within a range of $\Delta t \pm 15$ minutes. Prediction accuracy reached up to 95% within a time margin of $\pm 20$ minutes.

When considering both PP peak glucose level and time values, the prediction accuracy reached 87% with a range of $\Delta G \pm 20\%$ and $\Delta t \pm 15$ minutes, and even reached up to 90% within a range of $\Delta G \pm 20\%$ and $\Delta t \pm 20$ minutes.

Figure 10:
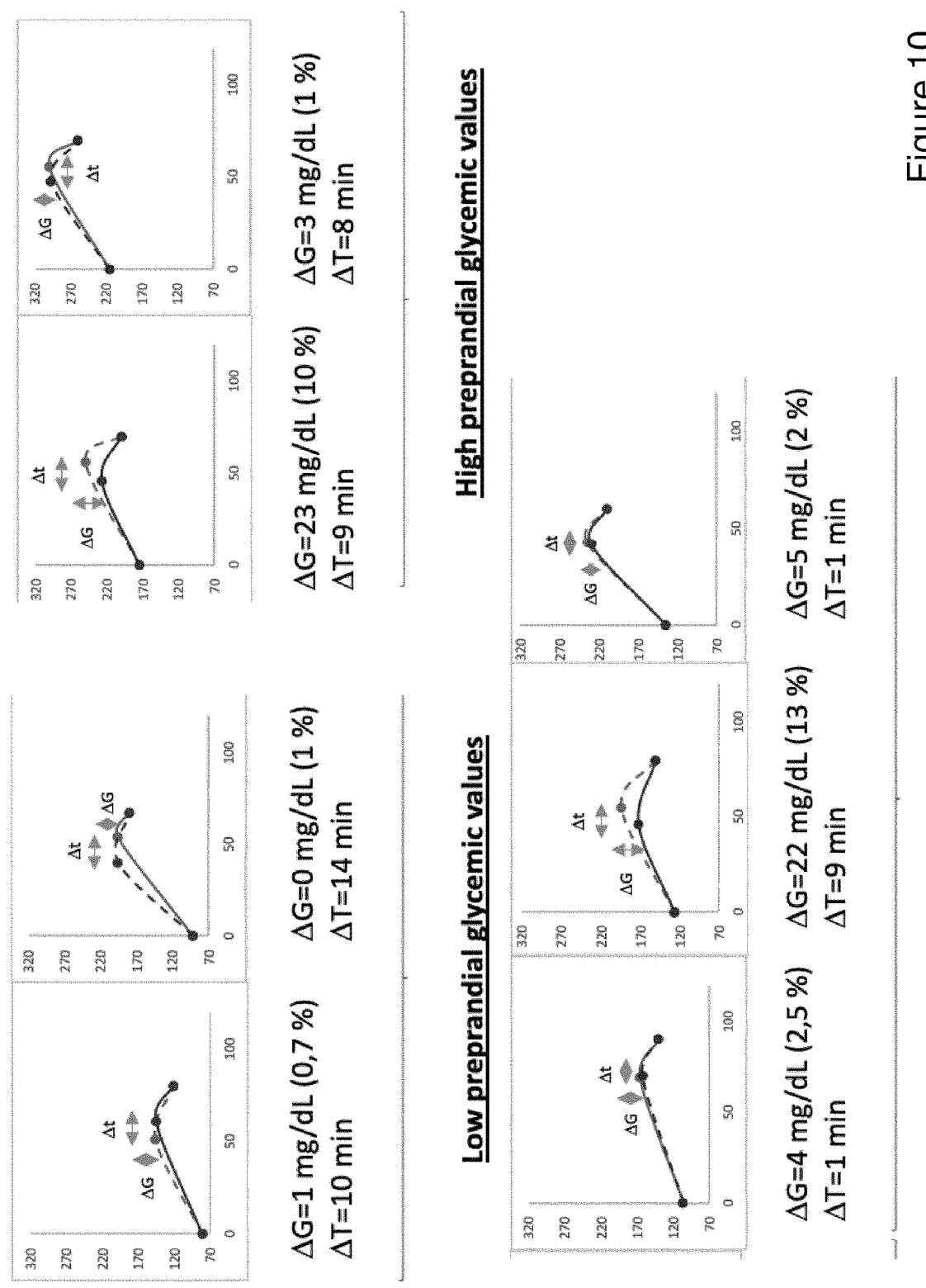
FIG. 10 illustrates the independence of the prediction method according to embodiments of the invention to preprandial glycemic values, based on first experiment data.

Of importance, the prediction of the algorithm value does not depend on the initial range of the pre-prandial glycemic values (i.e. $g_0$ measured when starting the meal). This is illustrated by FIG. 10 which reports the prediction error for low, normal and high pre-prandial glycemic values $g_0$. The predicted PP profile is shown in dotted line while the measured PP profile is shown in plain line.

The proposed postprandial glycemic peak prediction thus offers satisfying results.

Results and Discussion—Correlation Between the Accuracy of PP Peak Prediction and PP Profile Evolution Overtime No linear relation has been observed between Cf and $\Delta G$ when PP profile persists in the hyperglycemic range (FIG. 9 right side). It has then be hypothesized that an accurate PP peak prediction using the above algorithm is strongly correlated with meeting the recommended PP medical profiles.

Patient PP glycemic profiles (healthy profiles and PPH profiles) were thus analyzed by comparing the accuracy of the prediction values (peak glucose level and time) and the nature (healthy or PPH) of the profiles, i.e. their matching with the recommendations (i.e. whether a two-hour PP hyperglycemia occurred). The tables 4 and 5 below report the statistical results of the correlation between peak prediction and type of PP profiles. Various ranges of peak glucose level errors and peak time errors have been considered.

TABLE 4 correlation between peak prediction and PP profiles

|  | | Healthy profiles | | PPH profiles | |
|---|---|---|---|---|---|
| PP glycemic profiles | 85 | 39 | 46% | 46 | 54% |
| Accepted range of errors | | | | | |
| ΔG < [±20%] & Δt < [±20 min] | | | | | |
| Accurate prediction | 41 | 34 | 83% | 7 | 17% |
| Non-accurate prediction | 44 | 5 | 11% | 39 | 89% |
| ΔG < [±20%] & Δt < [±15 min] | | | | | |
| Accurate prediction | 38 | 32 | 84% | 6 | 16% |
| Non-accurate prediction | 47 | 7 | 15% | 40 | 85% |
| ΔG < [±15%] & Δt < [±20 min] | | | | | |
| Accurate prediction | 39 | 33 | 85% | 6 | 15% |
| Non-accurate prediction | 46 | 6 | 13% | 40 | 87% |
| ΔG < [±15%] & Δt < [±15 min] | | | | | |
| Accurate prediction | 37 | 31 | 84% | 6 | 16% |
| Non-accurate prediction | 48 | 8 | 17% | 40 | 83% |

TABLE 5

Accuracy, recall and precision depending of the accepted range of errors

| Accepted range of errors | | Healthy profiles | PPH profiles |
|---|---|---|---|
| ΔG < [±20%] & Δt < [±20 min] | Accuracy | 86% | |
| | Recall | 83% | 89% |
| | Precision | 87% | 85% |
| ΔG < [±20%] & Δt < [±15 min] | Accuracy | 85% | |
| | Recall | 84% | 85% |
| | Precision | 82% | 87% |
| ΔG < [±15%] & Δt < [±20 min] | Accuracy | 86% | |
| | Recall | 85% | 85% |
| | Precision | 85% | 87% |
| ΔG < [±15%] & Δt < [±15 min] | Accuracy | 84% | |
| | Recall | 84% | 83% |
| | Precision | 79% | 87% |

Depending on the accepted range of errors for ΔG and Δt, up to 83 to 85% of the healthy profiles had accurate predicted values while up to 87% of the PPH profiles had predicted values that were not accurate.

The number of non-accurate predictions associated with healthy profiles is minimal with the accepted range of errors of ΔG<[±20%] & Δt<[±20 min] and ΔG<[±15%] & Δt<[±20 min], with respectively 11 and 13% versus 15 and 17% for the accepted range of error of ΔG<[±20%] & Δt<[±15 min] and ΔG<[±15%] & Δt<[±15 min] respectively.

Accuracy, recall and precision were maximal when using the accepted range of errors of ΔG<[±20%] & Δt<[±20 min]

These results thus clearly show that an accurate peak prediction given a known error range is strongly correlated with a healthy profile, i.e. with low risks of two-hour PP hyperglycemia. On the other hand, an inaccurate peak prediction given a known error range is strongly correlated with a PPH profile, i.e. with high risks of two-hour or more (i.e. prolonged) PP hyperglycemia. In that case, a protocol of insulin delivery correction can be engaged.

Results and Discussion—Use of the Algorithm to Limit PP Hyperglycemic Phases

The above approach was used by patient 1 in real time with an accepted range of errors of ΔG<[±20%] & Δt<[±20 min] and a proposition of insulin delivery correction has been made based on the measured peak glucose level $g_{end}$ and a level of active insulin in the patient, $I_{active}$. The correction approach used considered providing 1.5 unit of insulin to decrease glycemic values by 30 mg/dL. The calculated need of insulin correction (correction=$I_{active}$-($g_{end}$-140)/30), if positive, was provided as follows:

an increase of the basal value when possible for one hour, with a total basal limit of two units/hour, and an insulin bolus for the remainder of insulin correction.

Figure 11:
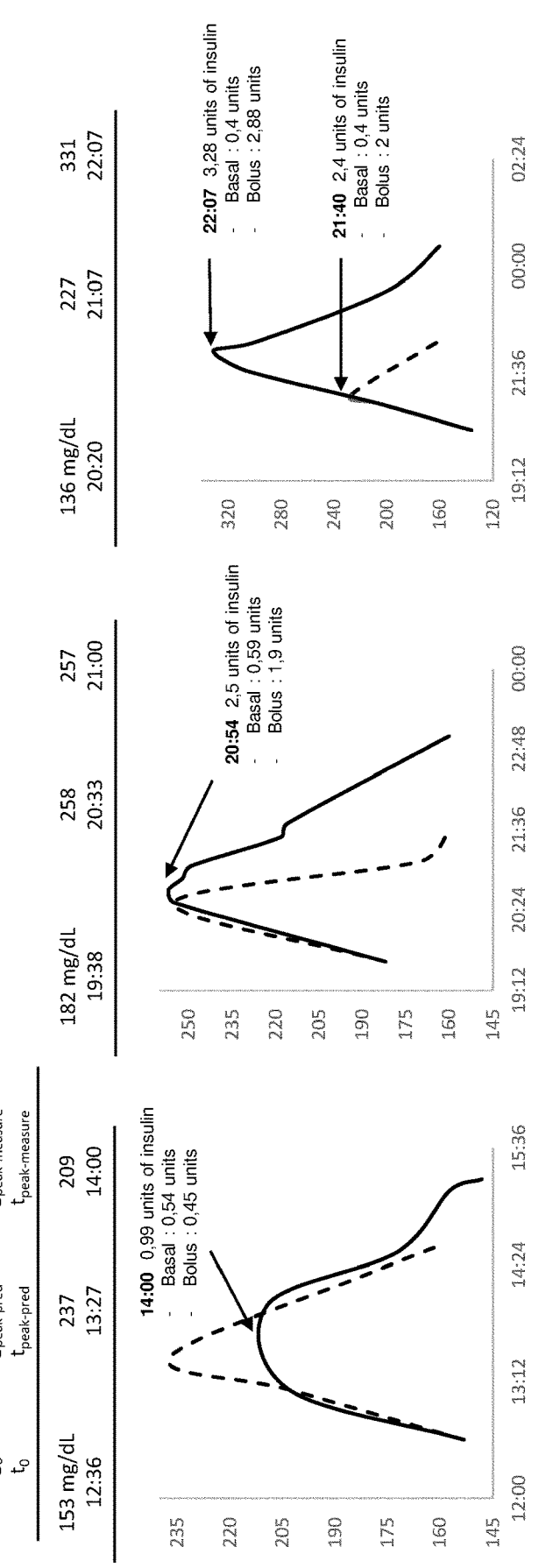
FIG. 11 illustrates three PP glucose profiles when insulin corrections according to first experiment data were made using the methods of the invention.

FIG. 11 illustrates three cases where insulin corrections were made for patient 1. The dotted plot represents the predicted PP glucose profile and the plain plot represents the measured PP glucose profile with insulin correction made due to detecting an inaccurate peak prediction using the invention.

For the first graphic, a pre-prandial glucose measurement was made at 12:36:153 mg/dL. The predicted peak was 237 mg/dl at 13:27, while the actual peak was 209 mg/dl at 14:00. The peak time error was higher than 20 min. Hence the peak prediction was considered inaccurate. A 0.99 unit insulin correction was thus made 84 minutes after the beginning of the meal as follows: 0.54 unit as basal and 0.45 unit as bolus. The actual PP glucose profile finally significantly decreased after the insulin correction, allowing to lower down the glucose level below the recommendations (160 mg/dL) with only a time shift of 34 minutes with respect to the two hour window of the recommendations.

Similarly, a 2.5 unit insulin correction was made in the second graphic 76 minutes after the beginning of the meal (0.59 unit as basal and 1.9 unit as bolus). The actual PP glucose profile lowered below 160 mg/dL with a time shift of 86 minutes.

Also, a 2.4 unit insulin correction was made in the third graphic 80 minutes after the beginning of the meal (0.4 unit as basal and 2 unit as bolus) followed by an additional insulin correction (3.28 units) 27 minutes later. The actual PP glucose profile lowered below 160 mg/dL with a time shift of 127 minutes.

Experiment 2

Protocol—Selected Patients

Case studies were conducted between April 2021 and March 2022 to confirm the above results of EXPERIMENT 1. Patients were selected at the discretion of the investigator according to the following inclusion/exclusion criteria:

Inclusion criteria: (1) 12-year-old or older man or woman; (2) patient with documented and stable type 1 diabetes with reasonable metabolic control at least every four months (Hemoglobin A1c levels<12%).

Exclusion criteria: (1) patient with no continuous glucose monitoring system, CGMS; (2) condition(s) other than diabetes compromising the safety of the patient (bulimia, anorexia, . . . ); (3) patient undergoing dialysis; (4) patient with known alcohol or drug dependency or abuse.

The selected patients were informed about the study and accepted the protocol in confidence with the investigator. Patients were diagnosed with type 1 diabetes. Before being enrolled in the study, each patient underwent a thorough review of their medical history (i.e., years since diagnosis, diabetes complications, HbA1c level), as summarized in the following table. "P" stands for patient identifier, "G" for gender, "A" for age in years, "DA" for diabetes age in years, "ODC" for others diabetic complications.

The selected patients were informed about the study and accepted the protocol in confidence with the investigator. Patients were diagnosed with type 1 diabetes. Before being enrolled in the study, each patient underwent a thorough review of their medical history (i.e., years since diagnosis, diabetes complications, HbA1c level), as summarized in the following table. "P" stands for patient identifier, "G" for gender, "A" for age in years, "DA" for diabetes age in years, "ODC" for others diabetic complications.

TABLE 1a

| | | | | | HbA1c | | | Insulin deliv. |
|---|---|---|---|---|---|---|---|---|
| P | G | A | DA | ODC | (%) | CGMS used | Insulin brand | device |
| 1 | F | 18 | 3 | None | 6.7-7.5 | DexcomG6 | Humalog ® (Lilly ®) | Pump Omnipod Dash ® |
| 2 | M | 46 | 5 | None | 6.9-7.5 | FreeStyle2 | FIASP ® (NovoNordisk ®) | Pump (Omnipod ®) |
| 3 | F | 24 | 22 | None | 6.0-6.5 | FreeStyle | Humalog ® (Lilly ®) Tresiba ® (NovoNordisk ®) | Pen |
| 4 | F | 45 | 2 | None | 6 | FreeStyle | None | None |
| 5 | M | 36 | 1 | None | 5.5 | FreeStyle2 | Novorapid ® (NovoNordisk ®) | Pump Omnipod Dash ® |
| 6 | M | 12 | 3 | None | 7.2 | FreeStyle | Novorapid ® Tresiba ® (NovoNordisk ®) | Pen NovoPen ® |
| 7 | F | 53 | 24 | None | 7.4 | FreeStyle | FIASP ® (NovoNordisk ®) | Pump Omnipod Dash ® |

In short, patient 1 was a 18 year-old woman with type 1 diabetes (HbA1c level comprised between 6.7% and 7.5%) diagnosed three years before the study. No other diabetic complications were reported during the study.

Patient 2 was a 45-year-old man with type 1 diabetes (HbA1c level comprised between 6.9% and 7.5%) diagnosed four years before the study. No other diabetic complications were reported during the study.

Patient 3 was a 25-year-old woman with type 1 diabetes (HbA1c level comprised between 6.0% and 6.5%) diagnosed at childhood. No other diabetic complications were reported during the study.

Patient 4 was a 43-year-old woman with type 1 diabetes (HbA1c level 6%) diagnosed two years before the study with no need of insulin administration. No other diabetic complications were reported during the study.

Patient 5 was a 12-year-old child with type 1 diabetes (HbA1c level 5.5%) diagnosed one year. No other diabetic complications were reported during the study.

Patient 6 was a 36-year-old man with type 1 diabetes (HbA1c level 7.2%) diagnosed three years before the study. No other diabetic complications were reported during the study.

Patient 7 was a 53-year-old man with type 1 diabetes (HbA1c level 7.4%) diagnosed 24 years before the study. No other diabetic complications were reported during the study.

Details of insulin brand and CGMS used for the various patients are reported in the Table above.

Protocol—Study

The study was divided into two subparts based on data to be assessed.

First subpart concerned the accuracy of the prediction of the postprandial (PP) peak, i.e. of the determination of both PP peak glucose and time values. For this, both blood glycemic values (i.e. glucose levels) were measured using continuous glucose monitoring system (CGMS) at the beginning of a complex meal and then 10-15 min after the end. Associated measuring times were recorded. These values were entered into the algorithm and a prediction of both PP peak glucose and time values ($g_{peak-pred}$, $t_{peak-pred}$) was calculated.

Second subpart checked the assumption that a strong correlation exists between the PP glucose profile and the accuracy of the PP peak prediction. PP glucose profiles, including real values for the PP peak, were extracted from data collected by the associated CGMS.

Finally, the algorithm was used to anticipate risks of prolonged PP hyperglycemia (i.e. more than two hours).

Note that few data from the patients were excluded from the analysis due to a non-respect of the study protocol.

Results and Discussion—Predictive Algorithm for PP Peaks

Glucose level measurements were continuously made by the CGMS from which the glucose increase ΔG of the postprandial peak was determined. Glucose increase ΔG corresponds to the difference between PP peak glycemic value (i.e. maximum glucose level) and the pre-prandial glycemic value measured just before starting the meal.

239 PP glucose profiles (i.e. 239 meals) were obtained from the 7 patients.

Similar to EXPERIMENT 1, the measured PP glucose profiles of the patients of EXPERIMENT 2 were classified into PP hyperglycemia (PPH) profiles (not meeting the International Diabetes Federation's recommendation to have a decreased glucose level below 160 mg/dl within two hours, i.e. showing a prolonged PPH superior beyond two hours) and PP healthy profiles (meeting the recommendation).

The following table summarizes this classification by counting up the PP healthy profiles from the 239 profiles.

TABLE 2a

| PPH profiles (EXPERIMENT 2) | | | |
|---|---|---|---|
| | # of meals | # healthy profiles | % |
| n | 239 | 134 | 56% |
| Patient P1 | 22 | 8 | 36% |
| Patient P2 | 12 | 5 | 42% |
| Patient P3 | 45 | 25 | 56% |
| Patient P4 | 34 | 22 | 65% |
| Patient P5 | 41 | 32 | 78% |
| Patient P6 | 40 | 21 | 53% |
| Patient P7 | 45 | 21 | 47% |

As shown in Table 2a, 56% of the measured profiles did reach the recommended medical values.

The distribution of slope Cf has thus be separately analyzed for the PPH profiles and the healthy profiles.

Similar to EXPERIMENT 1, FIG. 9a illustrates the distribution of slope Cf as a function of the PP glycemic increase ΔG for the 7 patients ('o' dots show new data for P1; '♦' dots show new data for P2; '•' dots show data for P3; 'x' dots show data for P4; 'Δ' dots show data for P5; '☐' dots show data for P6; '-' dots show data for P7). The plot on the left side corresponds to the distribution for healthy profiles only, while the plot on the right side corresponds to the distribution of the PPH only.

Similar to EXPERIMENT 1, the healthy profiles (left side) show a linear relationship between ΔG and Cf ($r^2=0.81$) while no linear relationship ($r^2=0.3$) has been identified with the PPH profiles. This confirms again that Cf can be calculated using two blood glucose level measurements and then ΔG can be obtained using the linear relationship, hence the PP peak can be predicted in few steps as explained above with respect to FIG. 4.

Similar to EXPERIMENT 1, the linear relationship between ΔG and Cf was calculated using linear regression on an initial subset of measurements from Patient 1, 2, 3 and 4 (the first 20% of the measured meals of 4 each patients).

The other measurements were used to validate the prediction accuracy.

The table below reports the accuracy of the peek prediction in terms of peak glucose level (shown through ΔG=glucose peak-$g_0$) and peak time (shown through Δt=peak time-$t_0$), for 79 healthy profiles, while considering a glucose margin of +/−20% and a time margin of +/−20 min.

TABLE 3a peak prediction accuracy (EXPERIMENT 2)

| | | | |
|---|---|---|---|
| Mean ΔG | 1.85 ± 17.08% | Mean Δt | 0.87 ± 16.1 min |
| RSME | 16.04% | RSME | 17.05 min |
| ΔG < [±20%] | 90% | Δt < [±20 min] | 90% |
| ΔG < [±20%] & Δt < [±20 min] | | 84% | |

As shown in the Table 3a, 90% of the measured PP peak glycemic blood values ($g_{peak-measure}$) matched the corresponding predicted ones ($g_{peak-pred}$) within a range of ΔG of ±20%. With respect to the peak time, 90% of the measured PP peak times ($t_{peak-measure}$) matched the corresponding predicted ones ($t_{peak-pred}$) within a range of Δt±20 minutes.

When considering both PP peak glucose level and time values, the prediction accuracy reached 84% with a range of ΔG±20% and Δt±20 minutes.

The proposed postprandial glycemic peak prediction thus offers satisfying results.

Results and Discussion—Correlation Between the Accuracy of PP Peak Prediction and PP Profile Evolution Overtime No linear relation has been observed between Cf and ΔG when PP profile persists in the hyperglycemic range (FIG. 9a right side). Similar to EXPERIMENT 1, it has been verified that an accurate PP peak prediction using the above algorithm is strongly correlated with meeting the recommended PP medical profiles.

Patient PP glycemic profiles (healthy profiles and PPH profiles) were thus analyzed by comparing the accuracy of the prediction values (peak glucose level and time) and the nature (healthy or PPH) of the profiles, i.e. their matching with the recommendations (i.e. whether a two-hour PP hyperglycemia occurred). The tables below report the statistical results of the correlation between peak prediction and type of PP profiles. Various ranges of peak glucose level errors and peak time errors have been considered.

TABLE 4a correlation between peak prediction and PP profiles (EXPERIMENT 2)

| | Healthy profiles | | PPH profiles | |
|---|---|---|---|---|
| PP glycemic profiles | 157 | 79 | 50.3% | 78 | 49.7% |
| Accepted range of errors ΔG < [±20%] & Δt < [±20 min] | | | | |
| Accurate prediction | 75 | 66 | 88% | 9 | 12% |
| Non-accurate prediction | 82 | 13 | 15.9% | 69 | 84.2% |

TABLE 5a

Accuracy, precision and recall of the algorithm.

| | Healthy profiles | PPH profiles |
|---|---|---|
| Accuracy | 86% | |
| Recall | 88% | 84% |
| Precision | 86% | 89% |

The best results were obtained when using the accepted range of errors of ΔG<[±20%] & Δt<[±20 min] with 88% of healthy profiles following accurate predictions and 84% of PPH profiles following not accurate predictions. Recall was of 88 and 84% for healthy and PPH profiles respectively. Precision was of 86 and 89% for healthy and PPH profiles respectively (Table 5a).

These results thus clearly show that an accurate peak prediction given the accepted error range ΔG<[±20%] & Δt<[±20 min] is strongly correlated with a healthy profile. On the other hand, an inaccurate peak prediction given the accepted error range ΔG<[±20%] & Δt<[±20 min] is strongly correlated with a PPH profile, i.e. with high risks of two-hour or more (i.e. prolonged) PP hyperglycemia. In that case, a protocol of insulin delivery correction can be engaged.

Experiment 3

Protocol—Selected Patients

Case studies were conducted between December 2021 and March 2022.

Patients were selected at the discretion of the investigator according to the following inclusion/exclusion criteria:

Inclusion criteria: (1) 18-year-old or older man or woman; (2) patient with documented and stable type 1 diabetes with reasonable metabolic control at least every four months (Hemoglobin A1c levels<12%).

Exclusion criteria: (1) patient with no continuous glucose monitoring system, CGMS; (2) condition(s) other than diabetes compromising the safety of the patient (bulimia, anorexia, . . . ); (3) patient undergoing dialysis; (4) patient with known alcohol or drug dependency or abuse.

The selected patients were informed about the study and accepted the protocol in confidence with the investigator. Patients were diagnosed with type 1 diabetes. Before being enrolled in the study, each patient underwent a thorough review of their medical history (i.e., years since diagnosis, diabetes complications, HbA1c level), as summarized in the following table. "P" stands for patient identifier, "G" for gender, "A" for age in years, "DA" for diabetes age in years, "ODC" for others diabetic complications.

TABLE 1b

| | | | | | HbA1c | | | Insulin deliv. |
| P | G | A | DA | ODC | (%) | CGMS used | Insulin brand | device |
|---|---|---|---|---|---|---|---|---|
| 1 | F | 33 | 10 | None | 6.9 | FreeStyle | Novorapid ® (NovoNordisk ®) | Pen |
| 2 | F | 67 | 13 | None | 8.6 | FreeStyle | FIASP ® (NovoNordisk ®) | Pump |
| 3 | H | 63 | 37 | None | 8.1 | FreeStyle | FIASP ® (NovoNordisk ®) | Pump |
| 4 | F | 45 | 28 | None | 6.9 | FreeStyle | FIASP ® (NovoNordisk ®) | Pump |
| 5 | F | 25 | 23 | None | 6 | FreeStyle2 | Novorapid ® (NovoNordisk ®) | Pump |
| 6 | H | 30 | 12 | None | 7.8 | FreeStyle | Novorapid ® (NovoNordisk ®) | Pen |
| 7 | H | 33 | 24 | None | 6 | FreeStyle | Novorapid ® (NovoNordisk ®) | Pen | patient characteristic at baseline (EXPERIMENT 3)

In short, patient 1 was a 33-year-old woman with type 1 diabetes (HbA1c level 6.9%) diagnosed ten years before the study. No other diabetic complications were reported during the study. Details of insulin brand and CGMS used are reported in the table above.

Patient 2 was a 67-year-old woman with type 1 diabetes (HbA1c level 8.6%) diagnosed thirteen years before the study. No other diabetic complications were reported during the study. Details of insulin brand and CGMS used are reported in the table above.

Patient 3 was a 63-year-old man with type 1 diabetes (HbA1c level 8.1%) diagnosed thirty-seven years before the study. No other diabetic complications were reported during the study. Details of insulin brand and CGMS used are reported in the Table above.

Patient 4 was a 45-year-old woman with type 1 diabetes (HbA1c level 6.9%) diagnosed twenty-eight years before the study. No other diabetic complications were reported during the study. Details of the CGMS used are reported in the Table above.

Patient 5 was a twenty-five-year-old woman with type 1 diabetes (HbA1c level 6%) diagnosed at childhood. No other diabetic complications were reported during the study. Details of the CGMS used are reported in the Table above.

Patient 6 was a 30-year-old man with type 1 diabetes (HbA1c level 7.8%) diagnosed twelve years before the study. No other diabetic complications were reported during the study. Details of the CGMS used are reported in the Table above.

Patient 7 was a 33-year-old man with type 1 diabetes (HbA1c level 6%) diagnosed 24 years before the study. No other diabetic complications were reported during the study. Details of the CGMS used are reported in the Table above.

Protocol—Study

The study was divided into two subparts based on data to be assessed.

First subpart concerned the accuracy of the prediction of the postprandial (PP) peak, i.e. of the determination of both PP peak glucose and time values. For this, both blood glycemic values (i.e. glucose levels) were measured using continuous glucose monitoring system (CGMS) at the beginning of a complex meal and then 10-15 min after the end. Associated measuring times were recorded. These values were entered into the algorithm and a prediction of both PP peak glucose and time values ($g_{peak-pred}$, $t_{peak-pred}$) was calculated.

Second subpart checked the assumption that a strong correlation exists between the PP glucose profile and the accuracy of the PP peak prediction. PP glucose profiles, including real values for the PP peak, were extracted from data collected by the associated CGMS.

Finally, the algorithm was used to anticipate risks of prolonged PP hyperglycemia (i.e. more than two hours).

Note that few data from the patients were excluded from the analysis due to a non-respect of the study protocol.

Results and Discussion—Predictive Algorithm for PP Peaks

Glucose level measurements were continuously made by the CGMS from which the glucose increase $\Delta G$ of the postprandial peak was determined. Glucose increase $\Delta G$ corresponds to the difference between PP peak glycemic value (i.e. maximum glucose level) and the pre-prandial glycemic value measured just before starting the meal.

234 PP glucose profiles (i.e. 234 meals) were obtained from the 7 patients.

Similar to EXPERIMENT 1 and EXPERIMENT 2, the measured PP glucose profiles of the patients of EXPERIMENT 3 were classified into PP hyperglycemia (PPH) profiles (not meeting the International Diabetes Federation's recommendation to have a decreased glucose level below 160 mg/dl within two hours, i.e. showing a prolonged PPH superior beyond two hours) and PP healthy profiles (meeting the recommendation).

The following table summarizes this classification by counting up the PP healthy profiles from the 234 profiles.

TABLE 2b

PPH profiles (EXPERIMENT 3)

| | # of meals | # healthy profiles | % |
|---|---|---|---|
| n | 234 | 139 | 59% |
| Patient PA | 30 | 11 | 37% |
| Patient PB | 40 | 19 | 48% |
| Patient PC | 30 | 23 | 77% |
| Patient PD | 37 | 25 | 68% |
| Patient PE | 32 | 24 | 75% |
| Patient PF | 30 | 17 | 57% |
| Patient PG | 35 | 20 | 57% |

As shown in Table 2b, 59% of the measured profiles did reach the recommended medical values.

The distribution of slope Cf has thus be separately analyzed for the PPH profiles and the healthy profiles.

Figure 9B:
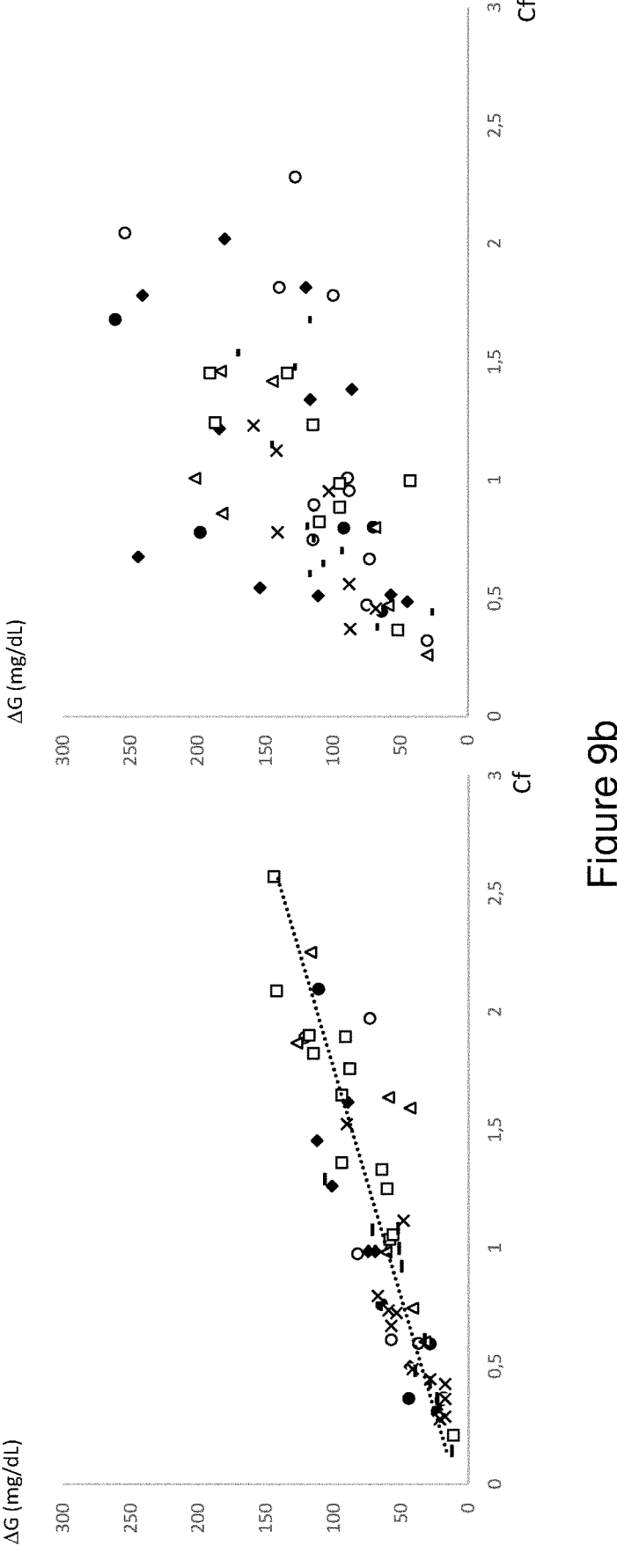
FIG. 9b illustrates the distribution of the PP peak glycemic increase ΔG as a function of rise rate Cf according to third experiment data.

Similar to EXPERIMENT 1 and EXPERIMENT 2, FIG. 9b illustrates the distribution of slope Cf as a function of the PP glycemic increase DG for the 7 patients ('o' dots show data for PA; '♦' dots show data for PB; '•' dots show data for PC; 'x' dots show data for PD; 'Δ' dots show data for PE; '☐' dots show data for PF; '-' dots show data for PG). The plot on the left side corresponds to the distribution for healthy profiles only, while the plot on the right side corresponds to the distribution of the PPH only.

Similar to EXPERIMENT 1&2, the healthy profiles (left side) show a linear relationship between ΔG and Cf ($r^2$=0.81) while no linear relationship ($r^2$=0.35) has been identified with the PPH profiles. This confirms Cf can be calculated using two blood glucose level measurements and then ΔG can be obtained using the linear relationship, hence the PP peak can be predicted in few steps as explained above with respect to FIG. 4.

Similar to EXPERIMENT 2, the linear relationship between ΔG and Cf was calculated using linear regression on an initial subset of measurements from Patient P1, P2, P3 and P4 (the first 20% of the measured meals from EXPERIMENT 2).

The table below reports the accuracy of the peek prediction in terms of peak glucose level (shown through ΔG=peak glucose-$g_0$) and peak time (shown through Δt=peak time-$t_0$), for 79 healthy profiles.

TABLE 3b

| peak prediction accuracy (EXPERIMENT 3) | | | |
|---|---|---|---|
| Mean ΔG | 4.78 ± 15.39% | Mean Δt | 1.83 ± 18.49 min |
| RSME | 15.97% | RSME | 18.40 min |
| ΔG < [±20%] | 85% | Δt < [±20 min] | 85% |
| ΔG < [±20%] & Δt < [±20 min] | | 80% | |

As shown in the Table 3b, 85% of the measured PP peak glycemic blood values ($g_{peak\text{-}measure}$) matched the corresponding predicted ones ($g_{peak\text{-}pred}$) within a range of ΔG of ±20%. With respect to the peak time, 85% of the measured PP peak times (peak-measure) matched the corresponding predicted ones ($t_{peak\text{-}pred}$) within a range of Δt±20 minutes.

When considering both PP peak glucose level and time values, the prediction accuracy reached 80% with a range of ΔG±20% and Δt±20 minutes.

The proposed postprandial glycemic peak prediction thus offers satisfying results.

Results and Discussion—Correlation Between the Accuracy of PP Peak Prediction and PP Profile Evolution Overtime No linear relation has been observed between Cf and ΔG when PP profile persists in the hyperglycemic range (FIG. 9b right side). Similar to EXPERIMENT 1&2, it has been verified that an accurate PP peak prediction using the above algorithm is strongly correlated with meeting the recommended PP medical profiles.

Patient PP glycemic profiles (healthy profiles and PPH profiles) were thus analyzed by comparing the accuracy of the prediction values (peak glucose level and time) and the nature (healthy or PPH) of the profiles, i.e. their matching with the recommendations (i.e. whether a two-hour PP hyperglycemia occurred). The table below reports the statistical results of the correlation between peak prediction and type of PP profiles. Various ranges of peak glucose level errors and peak time errors have been considered.

TABLE 4b

| correlation between peak prediction and PP profiles (EXPERIMENT 3) | | | | | |
|---|---|---|---|---|---|
| | | Healthy profiles | | PPH profiles | |
| PP glycemic profiles Accepted range of errors ΔG < [±20%] & Δt < [±20 min] | 125 | 60 | 48% | 65 | 52% |
| Accurate prediction | 50 | 48 | 96% | 2 | 4% |
| Non-accurate prediction | 75 | 12 | 16% | 63 | 84% |

The best results were obtained when using the accepted range of errors of ΔG<[±20%] & Δt<[±20 min] with 96% of healthy profiles following accurate predictions and 84% of PPH profiles following not accurate predictions. Recall was of 96 and 84% for healthy and PPH profiles respectively. Precision was of 80 and 97% for healthy and PPH profiles respectively (Table 5b).

TABLE 5b

| Accuracy, precision and recall of the algorithm. | | |
|---|---|---|
| | Healthy profiles | PPH profiles |
| Accuracy | 89% | |
| Recall | 96% | 84% |
| Precision | 80% | 97% |

These results thus clearly show that an accurate peak prediction given the accepted error range ΔG<[±20%] & Δt<[±20 min] is strongly correlated with a healthy profile. On the other hand, an inaccurate peak prediction given the accepted error range ΔG<[±20%] & Δt<[±20 min] is strongly correlated with a PPH profile, i.e. with high risks of two-hour or more (i.e. prolonged) PP hyperglycemia. In that case, a protocol of insulin delivery correction can be engaged.

Although the present invention has been described herein above with reference to specific embodiments, the present invention is not limited to the specific embodiments, and modifications will be apparent to a skilled person in the art which lie within the scope of the present invention.

Many further modifications and variations will suggest themselves to those versed in the art upon referring to the foregoing illustrative embodiments, which are given by way of example only and which are not intended to limit the scope of the invention, that being determined solely by the appended claims. In particular, the different features from different embodiments may be interchanged, where appropriate.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used.

The invention claimed is:

1. A computer-aided method of predicting a postprandial glycemic peak of an individual and adjusting insulin delivery to the individual, comprising:

obtaining, from a glucose sensor, blood glucose level measurements of the individual, including one pre-prandial blood glucose level measurement, determining a postprandial glucose change rate from the pre-prandial blood glucose level measurement and one postprandial blood glucose level measurement, based on a linear inference, determining a peak glucose level from the determined postprandial glucose change rate and from the pre-prandial blood glucose level measurement, and issuing, based on the inferred peak glucose level, a control signal to an insulin delivery device to adjust insulin delivery to the individual.

2. The method of claim 1, wherein the postprandial glucose change rate is determined from the pre-prandial blood glucose level measurement and only one postprandial blood glucose level measurement.

3. The method of claim 2, wherein a peak glucose increase is linearly inferred from the determined postprandial glucose change rate and the peak glucose level is a sum of the pre-prandial blood glucose level measurement with the peak glucose increase.

4. The method of claim 3, wherein a peak time is determined that is a sum of a ratio between the peak glucose increase and the postprandial glucose change rate with a pre-prandial time of the pre-prandial blood glucose level measurement.

5. The method of claim 1, wherein a peak glucose increase is linearly inferred from the determined postprandial glucose change rate, and the peak glucose level is a sum of the pre-prandial blood glucose level measurement with the peak glucose increase.

6. The method of claim 5, wherein a peak time is determined that is a sum of a ratio between the peak glucose increase and the postprandial glucose change rate with a pre-prandial time of the pre-prandial blood glucose level measurement.

7. A method of assisting a diabetic individual in managing insulin delivery, using a glucose sensor and measurements of blood glucose levels of the individual, the method comprising:

computer-predicting a postprandial peak glucose level using the method of claim 1, determining whether additional blood glucose level measurements include a measured postprandial peak glucose level matching the predicted postprandial peak glucose level, and in response to a determination that the measured postprandial peak glucose level does not match the predicted postprandial peak glucose level, issuing a control signal to an insulin delivery device to adjust insulin delivery to the individual.

8. The method of claim 7, wherein determining whether the measured postprandial peak glucose level matches the predicted postprandial peak glucose level includes determining whether a determined peak time of the measured postprandial peak glucose level equals a predicted peak time of the predicted postprandial peak glucose level given a time margin, and/or whether the measured postprandial peak glucose level equals the predicted postprandial peak glucose level given a glucose margin.

9. The method of claim 8, wherein the glucose margin is at least +/−5% and at most +/−25% of the predicted postprandial peak glucose level or the measured postprandial peak glucose level.

10. The method of claim 9, wherein the time margin is at least +/−5 min and at most +/−25 min.

11. The method of claim 9, wherein the measured postprandial peak glucose level and determined peak time respectively correspond to a local maximum blood glucose level measured during a postprandial time period and to a corresponding measurement time.

12. The method of claim 8, wherein the time margin is at least +/−5 min and at most +/−25 min.

13. The method of claim 8, wherein the measured postprandial peak glucose level and determined peak time respectively correspond to a local maximum blood glucose level measured during a postprandial time period and to a corresponding measurement time.

14. The method of claim 8, wherein the glucose margin is at least +/−15% and at most +/−20% of the predicted postprandial peak glucose level or the measured postprandial peak glucose level.

15. The method of claim 8, wherein the time margin is at least +/−15 min and at most +/−20 min.

16. A non-transitory computer-readable medium storing a program which, when executed by a microprocessor or computer system in a device, causes the device to perform the method of claim 1.

17. A computer device comprising:

a glucose sensor configured to obtain blood glucose level measurements of an individual, including one pre-prandial blood glucose level measurement, a postprandial glycemia rate unit configured to determine a postprandial glucose change rate from the pre-prandial blood glucose level measurement and one postprandial blood glucose level measurement, a peak determination unit configured to use linear inference to determine a peak glucose level from the determined postprandial glucose change rate and from the pre-prandial blood glucose level measurement, and an insulin delivery device configured to receive a control signal based on the determined peak glucose level and to adjust insulin delivery to the individual in response thereto.

18. The computer device of claim 17, wherein the postprandial glycemia rate unit is configured to determine the postprandial glucose change rate from the pre-prandial blood glucose level measurement and only one postprandial blood glucose level measurement.

19. A system comprising:

a computer device according to claim 17 configured to predict a postprandial glycemic peak based on some blood glucose level measurements, a matching peak determination unit configured to determine whether additional blood glucose level measurements include a measured postprandial glycemic peak matching the predicted postprandial glycemic peak, and a signal emitting unit configured to, in response to a determination that the measured postprandial glycemic peak does not match the predicted postprandial glycemic peak, issue the control signal to the insulin delivery device to adjust insulin delivery to the individual.

20. A non-transitory computer-readable medium storing a program which, when executed by a microprocessor or computer system in a device, causes the device to perform the method of claim 7.

* * * * *